(12) United States Patent
Burckhardt et al.

(10) Patent No.: US 10,100,068 B2
(45) Date of Patent: Oct. 16, 2018

(54) AMIDINE GROUP—OR GUANIDINE GROUP—CONTAINING SILANE

(71) Applicant: SIKA TECHNOLOGY AG, Baar (CH)

(72) Inventors: Urs Burckhardt, Zürich (CH); Rita Cannas, Dübendorf (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

(21) Appl. No.: 15/300,842

(22) PCT Filed: Apr. 16, 2015

(86) PCT No.: PCT/EP2015/058333
§ 371 (c)(1),
(2) Date: Sep. 30, 2016

(87) PCT Pub. No.: WO2015/158864
PCT Pub. Date: Oct. 22, 2015

(65) Prior Publication Data
US 2017/0081348 A1 Mar. 23, 2017

(30) Foreign Application Priority Data

Apr. 16, 2014 (EP) .................................... 14164920

(51) Int. Cl.
| | | |
|---|---|---|
| C07F 7/18 | (2006.01) | |
| C08G 77/26 | (2006.01) | |
| C08G 77/388 | (2006.01) | |
| B01J 31/00 | (2006.01) | |
| C07C 279/04 | (2006.01) | |
| C07C 279/12 | (2006.01) | |
| C07C 279/16 | (2006.01) | |
| C07C 279/18 | (2006.01) | |
| C08G 65/00 | (2006.01) | |
| C08G 77/08 | (2006.01) | |
| C09D 183/08 | (2006.01) | |
| C09J 183/08 | (2006.01) | |

(52) U.S. Cl.
CPC .............. *C07F 7/1844* (2013.01); *B01J 31/00* (2013.01); *C07C 279/04* (2013.01); *C07C 279/12* (2013.01); *C07C 279/16* (2013.01); *C07C 279/18* (2013.01); *C07F 7/1836* (2013.01); *C08G 65/002* (2013.01); *C08G 77/08* (2013.01); *C08G 77/26* (2013.01); *C08G 77/388* (2013.01); *C09D 183/08* (2013.01); *C09J 183/08* (2013.01); *C07C 2601/14* (2017.05)

(58) Field of Classification Search
CPC ............................... C07F 7/081; C07F 7/0812
See application file for complete search history.

(56) References Cited

U.S. PATENT DOCUMENTS

| | | |
|---|---|---|
| 2011/0046299 A1 | 2/2011 | Malivemey et al. |
| 2011/0098392 A1 | 4/2011 | Barrandon et al. |

FOREIGN PATENT DOCUMENTS

| | | |
|---|---|---|
| CN | 101998960 A | 3/2011 |
| CN | 103408940 A | 11/2013 |
| FR | 2925496 A1 | 6/2009 |
| JP | 2002-167438 A | 6/2002 |

OTHER PUBLICATIONS

Koech (RSC Advances (2013) 3(2) 566-572).*
Albert (Tetrahedron Letters (1989) 30(43) 5945-8).*
Sep. 18, 2017 Office Action issued in Chinese Patent Application No. 201580019699.9.
Jun. 8, 2015 International Search Report issued in International Patent Application No. PCT/EP2015/058333.
May 31, 2018 Office Action issued in Chinese Application No. 201580019699.9.

* cited by examiner

*Primary Examiner* — Kuo Liang Peng
(74) *Attorney, Agent, or Firm* — Oliff PLC

(57) ABSTRACT

A silane of the formula (I) containing at least one aliphatic amidine group- or guanidine group-containing alkoxy group, to a method for producing same, to conversion products thereof, and to the use thereof as a catalyst in curable compositions, in particular based on silane group-containing polymers. The silane of the formula (I) is largely odorless and non-volatile at room temperature. The silane accelerates the hydrolysis and condensation reaction of silane groups very effectively without impairing the storage stability of silane group-containing polymers. Additionally, the silane is very tolerable in silane group-containing compositions, whereby such compositions are not prone to separate, migrate, or evaporate the catalyst.

15 Claims, No Drawings

AMIDINE GROUP—OR GUANIDINE GROUP—CONTAINING SILANE

TECHNICAL FIELD

The invention relates to silanes containing amidine or guanidine groups and to the use thereof as catalysts for the crosslinking of curable compositions.

PRIOR ART

Curable compositions play a significant part in numerous industrial applications, as adhesives, sealants or coatings, for example. Their curing is brought about by crosslinking reactions, which proceed by way of free or latent reactive groups such as, for example, isocyanate groups, epoxide groups, hydroxyl groups, amino groups or silane groups, these groups reacting with themselves or with one another, after a mixing operation, by heating or by contact with moisture, and so connecting the structural components present in the composition covalently to form a polymeric network. Catalysts are frequently used in order to accelerate such crosslinking reactions. Very often these catalysts are toxicologically objectionable compounds, posing a potential hazard to workers and environment, particularly after the curing of the composition, when the catalyst or its breakdown products are released by outgassing, migration or leaching.

Compositions curable at room temperature and based on polymers containing silane groups are especially confronted with this problem scenario. Polymers containing silane groups are in this context, in particular, polyorganosilanes, referred to commonly as "silicones" or "silicone rubbers", and organic polymers containing silane groups, which are also referred to as "silane-functional polymers", "silane-modified polymers" (SMP) or "silane-terminated polymers" (STP). Their crosslinking proceeds via the condensation of silanol groups, with formation of siloxane bonds, and is conventionally catalyzed by means of organotin compounds, such as dialkyltin(IV) carboxylates in particular. These catalysts are notable for a very high activity in relation to the silanol condensation, and are very resistant to hydrolysis; however, they are harmful to health and a great hazard to water. Oftentimes they are combined with further catalysts, primarily with basic compounds such as, in particular, amines, which above all accelerate the prior hydrolysis of the silane groups. On account of a greater weighting given to EHS issues by professional associations and consumers, and also in the view of more stringent state regulation, efforts have been undertaken to an increased extent for some time to replace the organotin compounds by alternative, less toxic catalysts. Hence, for instance, organotitanates, organozirconates and organoaluminates have been described by way of alternative metal catalysts. These catalysts, however, usually have a lower catalytic activity in relation to the silanol condensation, and produce much slower crosslinking. On account of their lack of stability toward hydrolysis, they may lose a major part of their activity during storage of the composition, by residual moisture in the ingredients, thereby causing curing to slow down greatly or to come to a standstill completely. Another known alternative to organotin compounds is represented by strongly basic nitrogen compounds from the class of amidines and guanidines, which can be used in combination with the aforementioned metal catalysts or else on their own. Many of the commonplace amidine and guanidine catalysts, such as, in particular, 1,8-diazabicyclo[5.4.0]undec-7-ene (DBU) and 1,1,3,3-tetramethylguanidine (TMG), however, are volatile compounds with an intense odor which are likewise harmful to health and hazardous to the environment. Furthermore, they have a tendency to migrate in the composition, owing to poor compatibility, and so to give rise to separation, exudation or substrate fouling. The described use of aromatic amidines and guanidines which are solid at room temperature provides a remedy here, but requires the use of appropriate solvents and is accompanied by detractions from the catalytic activity and hence from the crosslinking rate.

SUMMARY OF THE INVENTION

It is an object of the present invention, therefore, to provide a catalyst for the crosslinking of curable compositions, especially compositions containing silane groups, which possesses a high catalytic activity for the crosslinking reaction and so permits rapid curing of the applied composition, and which also exhibits a high selectivity for this crosslinking reaction and therefore does not excessively detract from the storage stability of the composition. The catalyst, moreover, is to have a low vapor pressure and a high compatibility with the composition, so that it tends neither toward separation or migration nor toward evaporation, and is as far as possible to be odorless and of low toxicity. This object is achieved by a silane containing amidine or guanidine groups as claimed in claim 1. The silane as claimed in claim 1 comprises at least one alkoxy radical with an aliphatic amidine or guanidine group, and exhibits high catalytic activity, whereas aromatic compounds containing amidine or guanidine groups have virtually no catalytic activity or none at all. In contrast to many aliphatic amidine or guanidine catalysts known from the prior art, it is largely odorless and nonvolatile at room temperature. It displays a high catalytic activity and good selectivity. This is particularly surprising since in view of its relatively high molecular weight, the expectation would still be of a reduced activity as compared with smaller and hence more mobile amidines or guanidines. Relative to the use of amidines or guanidines containing hydroxyl groups, it has a variety of advantages. The silanes as claimed in claim 1 are typically liquid and of low viscosity, which is beneficial to their use and metering, and especially in compositions which crosslink via silane groups, they are more catalytically active, and during the storage of such a composition they are unable to trigger any stability problems caused by free hydroxyl groups.

Moreover, the volatile organic compound (alcohol or ketoxime) released during the preparation of the silane as claimed in claim 1 can be removed in a targeted way, this being advantageous in the context of use in curable compositions, since the emission of volatile organic compounds therefrom is therefore reduced.

With these properties, the silane as claimed in claim 1 and/or a reaction product thereof containing amidine or guanidine groups is outstandingly suitable for use in compositions containing silane groups, where, as a sole catalyst or in combination with further catalysts, it enables rapid curing to form a mechanically high-grade and robust material, without adversely affecting the storage capacity of the uncured composition. Both before and after curing, it is outstandingly compatible with the composition and displays no tendency either toward separation or toward migration, unlike many similar compositions with amidine and guanidine catalysts according to the prior art, where catalyst-induced migration effects play a major role. It allows low-emission and low-odor products which neither exhibit greasy or sticky surfaces nor give rise to substrate fouling. Lastly, the silane as claimed in claim 1 can be prepared in a surprisingly simple and rapid process, without auxiliaries, from commercially customary, inexpensive starting materials.

Further aspects of the invention are the subject of further independent claims. Particularly preferred embodiments of the invention are subjects of the dependent claims.

CERTAIN EMBODIMENTS OF THE INVENTION

A subject of the invention is a silane of the formula (I), in which

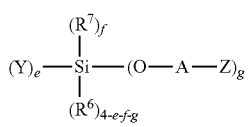
(I)

Z is an amidine or guanidine group bonded via a nitrogen atom,

A is a divalent aliphatic or cycloaliphatic or arylaliphatic hydrocarbon radical having 2 to 20 C atoms, which optionally comprises ether-oxygen or secondary or tertiary amine-nitrogen, e is 0 or 1, f is 0 or 1 or 2, and g is an integer from 1 to 4, and the sum (e+f+g) is an integer from 1 to 4, $R^6$ either is an alkoxy radical having 1 to 12 C atoms which optionally contains ether-oxygen, or is a ketoximato radical having 1 to 13 C atoms, $R^7$ is a monovalent hydrocarbon radical having 1 to 12 C atoms, and Y is a monovalent hydrocarbon radical having 1 to 20 C atoms which optionally has a terminal mercapto group, epoxide group, (meth)acryloyl group, amidine group, guanidine group, urethane group or urea group or has a terminal amino group of the formula —$NHR^8$, and which optionally contains ether-oxygen or secondary amine-nitrogen, where $R^8$ is a hydrogen radical or an alkyl or cycloalkyl or aralkyl radical having 1 to 8 C atoms or is a radical

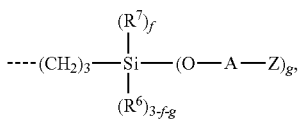

where the silane of the formula (I) contains no nitrogen atom which is bonded directly to an aromatic ring or is part of a heteroaromatic ring system, such as imidazole or pyrimidine, for example.

In the present document, the term "silane group" identifies a silyl group which is bonded to an organic radical or to a polyorganosilane radical and which has one to three, more particularly two or three, hydrolyzable substituents on the silicon atom. Particularly commonplace hydrolyzable substituents are alkoxy radicals. These silane groups are also referred to as "alkoxysilane groups". Silane groups may also be present in partially or fully hydrolyzed form. "Hydroxysilane", "isocyanatosilane", "aminosilane" or "mercaptosilane" refers to organoalkoxysilanes which on the organic radical, in addition to the silane group, have one or more hydroxyl, isocyanato, amino or mercapto groups, respectively.

A "primary amino group" or "primary amine-nitrogen" is an $NH_2$ group or its nitrogen atom which is bonded to an organic radical, and a "secondary amino group" or "secondary amine-nitrogen" is an NH group or its nitrogen atom which is bonded to two organic radicals, which may also together be part of a ring, and a "tertiary amino group" or "tertiary amine-nitrogen" is a N group or its nitrogen atom which is bonded to three organic radicals, of which two or three may also form part of one or more rings.

Substance names beginning with "poly" such as polyol or polyisocyanate refer to substances which formally contain two or more per molecule of the functional groups that occur in their name.

The term "organic polymer" encompasses a collective of chemically unitary macromolecules which nevertheless differ in terms of degree of polymerization, molar mass, and chain length, is collective having been prepared by a polymerization reaction (chain-growth polymerization, polyaddition, polycondensation) and having primarily carbon atoms in the polymer backbone, and also reaction products of a collective of macromolecules of this kind. Polymers having a polyorganosiloxane backbone (commonly referred to as "silicones") are not organic polymers for the purposes of the present document.

The term "polyether containing silane groups" also encompasses organic polymers containing silane groups and being also able, in addition to polyether units, to comprise urethane groups, urea groups or thiourethane groups. Polyethers of this kind containing silane groups may also be referred to as "polyurethanes containing silane groups".

"Molecular weight" is understood in the present document to refer to the molar mass (in grams per mole) of a molecule or of a part of a molecule, also referred to as "radical". "Average molecular weight" is the numerical average $M_n$ of an oligomeric or polymeric mixture of molecules or radicals, which is determined customarily by means of gel permeation chromatography (GPC) against polystyrene as standard.

"Storage-stable" or "storable" is an adjective applied to a substance or to a composition when it can be kept at room temperature in a suitable container for a relatively long time, typically at least 3 months up to 6 months or more, without any change in its application or service properties, particularly the viscosity and the crosslinking rate, as a result of the storage, to any extent relative to its usage.

A dashed line in the formula in this document represents in each case the bond between a substituent and the associated remainder of the molecule. "Room temperature" refers to a temperature of approximately 23° C.

The silane of the formula (I) may also be present in tautomeric form. All possible tautomeric forms of the silane of the formula (I) are considered equivalent for the purposes of the present invention.

Furthermore, the silane of the formula (I) can be present in protonated form. The silane of the formula (I) may likewise be present in complexed form, more particularly with cations of zinc, iron or molybdenum.

Preferably Z is

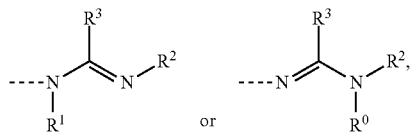 or 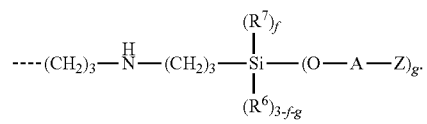

where
$R^0$ is a hydrogen radical or is an alkyl or cycloalkyl or aralkyl radical having 1 to 8 C atoms,
$R^1$ is a hydrogen radical or is an alkyl or cycloalkyl or aralkyl radical having 1 to 8 C atoms, or together with $R^2$ is $R^9$,
$R^2$ is a hydrogen radical or is an alkyl, cycloalkyl or aralkyl radical having 1 to 18 C atoms, which optionally contains ether-oxygen or tertiary amine-nitrogen, or together with $R^1$ is $R^9$,
$R^3$ is —$NR^4R^5$ or is a hydrogen radical or is an alkyl or cycloalkyl or aralkyl radical having 1 to 12 C atoms,
$R^4$ and $R^5$ independently of one another are each a hydrogen radical or are an alkyl, cycloalkyl or aralkyl radical having 1 to 18 C atoms, which optionally contains ether-oxygen or tertiary amine-nitrogen, and
$R^9$ is 1,2-ethylene or 1,2-propylene or 1,3-propylene or 1,3-butylene or 1,3-pentylene,
where
$R^2$ and $R^0$ may also together be an alkylene radical having 3 to 6 C atoms, which optionally contains ether-oxygen or tertiary amine-nitrogen,
$R^2$ and $R^3$ may also together be an alkylene radical having 3 to 6 C atoms,
$R^4$ and $R^5$ may also together be an alkylene radical having 4 to 7 C atoms, which optionally contains ether-oxygen or tertiary amine-nitrogen, and
$R^2$ and $R^5$ may also together be an alkylene radical having 2 to 12 C atoms.

A is preferably an alkylene radical having 2 to 10, more particularly 2 to 6, C atoms, which optionally contains one or two ether-oxygens.

More particularly, A is selected from the group consisting of 1,2-ethylene, 1,2-propylene, 1,3-propylene, 1,4-butylene, 1,1-dimethyl-1,2-ethylene, 1,5-pentylene, 1,6-hexylene, (1,5,5-trimethylcyclohexan-1-yl)methane-1,3,3-oxa-1,5-pentylene and 3,6-dioxa-1,8-octylene.

Preferably e is 0 or 1.
Preferably f is 0 or 1, more particularly 0.
Preferably $R^6$ is an alkoxy radical having 1 to 4 C atoms, which optionally contains one or two ether-oxygens, and more particularly is methoxy or ethoxy.

Further preferably, $R^6$ is a ketoximato radical having 1 to 6 C atoms, and more particularly is methylethylketoximato or methylisobutylketoximato.

Preferably $R^7$ is a monovalent hydrocarbon radical having 1 to 6 C atoms, and more particularly is a methyl radical or is a phenyl radical.

Preferably Y is a monovalent hydrocarbon radical having 1 to 8 C atoms, which optionally has a terminal mercapto group, epoxide group, (meth)acryloyl group, amidine group, guanidine group, urethane group or urea group or has a terminal amino group of the formula —$NHR^8$, and which optionally comprises an ether-oxygen or secondary amine-nitrogen.

More particularly Y is selected from the group consisting of methyl, octyl, isooctyl, phenyl, vinyl, 3-aminopropyl, N-(2-aminoethyl)-3-aminopropyl, 3-mercaptopropyl, 3-glycidyloxypropyl, 3-acryloyloxypropyl, 3-methacryloyloxypropyl, and a radical of the formula $$----(CH_2)_3—\overset{H}{N}—(CH_2)_3—\underset{(R^6)_{3-f-g}}{\overset{(R^7)_f}{Si}}—(O—A—Z)_g.$$

$R^0$ is preferably a hydrogen radical or is an alkyl radical having 1 to 4 C atoms, more particularly a hydrogen radical.
$R^1$ is preferably a hydrogen radical or is an alkyl or cycloalkyl or aralkyl radical having 1 to 4 C atoms, or together with $R^2$ is $R^9$.
$R^2$ is preferably an alkyl, cycloalkyl or aralkyl radical having 1 to 12, more particularly 1 to 8 C atoms, which optionally contains ether-oxygen or tertiary amine-nitrogen, or together with $R^1$ is $R^9$.
$R^3$ is preferably —$NR^4R^5$ or is a hydrogen radical or is an alkyl, cycloalkyl or aralkyl radical having 1 to 8, more particularly 1 to 4, C atoms.
$R^4$ and $R^5$ are preferably, independently of one another, in each case a hydrogen radical or are an alkyl, cycloalkyl or aralkyl radical having 1 to 12 C atoms, which optionally contains an ether-oxygen or a tertiary amine-nitrogen. Further preferably $R^4$ and $R^5$ together are an alkylene radical having 4 to 7 C atoms which optionally contains an ether-oxygen or a tertiary amine-nitrogen. More preferably $R^4$ is a hydrogen radical.

In one preferred embodiment Z is an amidine group. A silane of this kind is also referred to below as "amidinosilane of the formula (I)".
$R^3$ in this case is a hydrogen radical or is an alkyl, cycloalkyl or aralkyl radical having 1 to 12, preferably 1 to 8, more particularly 1 to 4, C atoms, or together with $R^2$ is an alkylene radical having 3 to 6, more particularly 3 to 5, C atoms. More preferably $R^3$ is a hydrogen radical or is a methyl radical, and more particularly is a methyl radical.

An amidinosilane of the formula (I) has the advantage that it does not have quite as high a catalytic activity and can therefore be used in a somewhat greater amount, so making it less susceptible to disruptions caused by other constituents of the composition, particularly the impurities present therein.

In one preferred amidinosilane of the formula (I), Z is

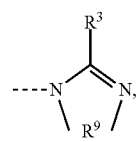

where $R^3$ and $R^9$ have the stated definitions.
More preferably $R^3$ is a hydrogen radical or is a methyl radical.
Preferably $R^9$ is 1,3-propylene.
Most preferably $R^3$ is methyl and $R^9$ is 1,3-propylene.
In another preferred embodiment, Z is a guanidine group. A silane of this kind is also referred to below as "guanidinosilane of the formula (I)".
In this case $R^3$ is —$NR^4R^5$.
Preferably $R^4$ is a hydrogen radical.

Preferably $R^5$ is an alkyl, cycloalkyl or aralkyl radical having 1 to 18 C atoms which optionally contains heteroatoms.

A guanidinosilane of the formula (I) has the advantage that it exhibits a particularly high catalytic activity.

In one preferred guanidinosilane of the formula (I), Z is

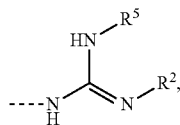

where $R^2$ and $R^5$ independently of one another are each alkyl, cycloalkyl or aralkyl radicals having 1 to 12 C atoms, which optionally contains ether-oxygen or tertiary amine-nitrogen.

Preferably here $R^2$ and $R^5$ independently of one another are each ethyl, isopropyl, tert-butyl, 3-(dimethylamino)propyl or cyclohexyl, and more particularly are isopropyl or cyclohexyl.

The preferred silanes of the formula (I) can be simply prepared from commercial, inexpensive raw materials, and exhibit high catalytic activity and compatibility in curable compositions, especially those based on polymers containing silane groups.

A further subject of the invention is a process for preparing the silane of the formula (I), where at least one amine of the formula (IIa) or (IIb), $$\text{HO-A-NHR}^1 \qquad \text{(IIa)}$$

$$\text{HO-A-NH—R}^9\text{—NH}_2 \qquad \text{(IIb)}$$

optionally at least one amine of the formula $R^2$—NH—$R^0$, where $R^0$ is a hydrogen radical or is an alkyl or cycloalkyl or aralkyl radical having 1 to 8 C atoms and $R^2$ is an alkyl, cycloalkyl or aralkyl radical having 1 to 18 C atoms, which optionally contains heteroatoms, or $R^0$ and $R^2$ together are an alkylene radical having 3 to 6 C atoms which optionally contains heteroatoms, at least one reagent for introducing amidine or guanidine groups, and at least one alkoxy- or ketoximato-silane are reacted with one another.

A, $R^1$, and $R^9$ here have the definitions already stated.

The reaction product from this process can be used without further workup as a catalyst for the crosslinking of a curable composition.

Suitability as amine of the formula (IIa) or (IIb) is possessed by aliphatic or cycloaliphatic or arylaliphatic hydroxylamines, more particularly 2-aminoethanol, 2-methylaminoethanol (2-amino-1-propanol), 1-amino-2-propanol, 3-amino-1-propanol, 4-amino-1-butanol, 4-amino-2-butanol, 2-amino-2-methylpropanol, 5-amino-1-pentanol, 6-amino-1-hexanol, 7-amino-1-heptanol, 8-amino-1-octanol, 10-amino-1-decanol, 12-amino-1-dodecanol, 4-(2-aminoethyl)-2-hydroxyethylbenzene, 3-aminomethyl-3,5,5-trimethylcyclohexanol, glycol derivatives which carry a primary amino group, such as diethylene glycol, dipropylene glycol, dibutylene glycol or higher oligomers or polymers of these glycols, more particularly 2-(2-aminoethoxy)ethanol, 2-(2-(2-aminoethoxy)ethoxy)ethanol, α-(2-hydroxymethylethyl)-ω-(2-aminomethylethoxy)poly(oxy(methyl-1,2-ethanediyl)), derivatives, carrying a hydroxyl group and a primary amino group, of polyalkoxylated alcohols with a hydricity of three or more, products from simple cyanoethylation and subsequent hydration of glycols, more particularly 3-(2-hydroxyethoxy)propylamine, 3-(2-(2-hydroxyethoxy)ethoxy)propylamine or 3-(6-hydroxyhexyloxy) propylamine, and also, furthermore, hydroxylamines having a primary and a secondary amino group, such as, in particular, N-(2-aminoethyl)-2-aminoethanol or N-(3-aminopropyl)-2-aminoethanol.

The amine of the formula (IIa) or (IIb) is preferably selected from the group consisting of 2-aminoethanol, 1-amino-2-propanol, 3-amino-1-propanol, 4-amino-1-butanol, 2-amino-2-methylpropanol, 5-amino-1-pentanol, 6-amino-1-hexanol, 3-aminomethyl-3,5,5-trimethylcyclohexanol, 2-(2-aminoethoxy)-ethanol, 2-(2-(2-aminoethoxy)ethoxy)ethanol, N-(2-aminoethyl)-2-aminoethanol and N-(3-aminopropyl)-2-aminoethanol.

Suitability as amine of formula $R^2$—NH—$R^0$ is possessed by aliphatic, cycloaliphatic or arylaliphatic monoamines, more particularly amines of the formula $R^2$—NH$_2$. Preferred are methylamine, ethylamine, propylamine, isopropylamine, n-butylamine, isobutylamine, sec-butylamine, n-hexylamine, cyclohexylamine, benzylamine, 2-ethylhexylamine, n-octylamine, n-decylamine, laurylamine or 2-methoxyethylamine.

The reagent for introducing amidine or guanidine groups is preferably selected from the group consisting of orthoesters, 1,3-keto esters, 1,3-keto amides, nitriles, imidic esters, imidic chlorides, amides, lactams, cyanamides, carbodiimides, ureas, O-alkylisoureas, thioureas, S-alkylisothioureas, aminoiminomethanesulfonic acids, guanylpyrazoles, and guanidines.

Suitability for the introduction of amidine groups is possessed by orthoesters, 1,3-keto esters, 1,3-keto amides, nitriles, imidic esters, imidic chlorides, amides or lactams. Preferred are orthoesters, 1,3-keto esters or nitriles.

Preferred orthoesters are orthoesters of the formula $R^3$—C(O$R^a$)$_3$, where $R^3$ has the stated definitions and $R^a$ is an alkyl radical having 1 to 4 C atoms.

Particularly suitable is an orthoformate, orthoacetate, orthopropionate, orthobutyrate or orthovalerate, more particularly trimethylorthoformate, triethyl orthoformate, trimethyl orthoacetate or triethyl orthoacetate.

Preferred 1,3-keto esters are 1,3-keto esters of the formula $R^3$—C(O)CH$_2$C(O)O$R^a$, where $R^3$ and $R^a$ have the definitions already stated, more particularly methyl acetoacetate, ethyl acetoacetate, isopropyl acetoacetate or tert-butyl acetoacetate, more preferably ethyl acetoacetate.

Preferred nitriles are nitriles of the formula $R^3$—CN, where $R^3$ has the stated definitions, more particularly acetonitrile, propionitrile, butyronitrile, isobutyronitrile, valeronitrile or capronitrile, more preferably acetonitrile.

Suitability for the introduction of guanidine groups is possessed by cyanamides, carbodiimides, ureas, O-alkylisoureas, thioureas, S-alkylisothioureas, aminoiminomethanesulfonic acids, guanylpyrazoles or guanidines. Preferred are cyanamides or carbodiimides, especially carbodiimides.

Preferred as carbodiimide are carbodiimides of the formula $R^5$N=C=N$R^2$, where $R^2$ and $R^5$ have the definitions already stated. Particularly preferred is N,N'-diisopropylcarbodiimide (DIC), N,N'-di-tert-butylcarbodiimide, N,N'-dicyclohexylcarbodiimide (DCC) or N-ethyl-N'-(3-dimethylaminopropyl)carbodiimide (EDC), more particularly N,N'-diisopropylcarbodiimide (DIC) or N,N'-dicyclohexylcarbodiimide (DCC).

The reagent for introducing amidine or guanidine groups is preferably selected from the group consisting of trimethyl orthoformate, triethyl orthoformate, trimethyl orthoacetate, triethyl orthoacetate, methyl acetoacetate, ethyl acetoacetate, isopropyl acetoacetate, tert-butyl acetoacetate, acetonitrile, N,N'-diisopropylcarbodiimide, N,N'-di-tert-butylcarbodiimide, N-ethyl-N'-(3-dimethylaminopropyl)carbodiimide, and N,N'-dicyclohexylcarbodiimide. Silanes having particularly high catalytic activity are obtained in a particularly simple way with these reagents.

Preferred alkoxy- or ketoximato silanes are orthosilicates, organoalkoxysilanes, organoketoximatosilanes, or silanes having alkoxy and ketoximato groups. The alkoxy- or ketoximato-silane is preferably selected from the group consisting of tetramethyl orthosilicate, tetraethyl orthosilicate, methyltrimethoxysilane, dimethyldimethoxysilane, ethyltrimethoxysilane, propyltrimethoxysilane, phenyltrimethoxysilane, phenyldimethoxymethylsilane, octyltrimethoxysilane, isooctyltrimethoxysilane, vinyltrimethoxysilane, vinyldimethoxymethylsilane, 3-aminopropyltrimethoxysilane, 3-aminopropyldimethoxymethylsilane, N-(2-aminoethyl)-3-aminopropyltrimethoxysilane, N-(2-aminoethyl)-3-aminopropyldimethoxymethylsilane, N,N-bis(trimethoxysilylpropyl)amine, 3-mercaptopropyltrimethoxysilane, 3-mercaptopropyldimethoxymethylsilane, 3-glycidyloxypropyltrimethoxysilane, 3-glycidyloxypropyldimethoxymethylsilane, 3-acryloyloxypropyltrimethoxysilane, 3-acryloyloxypropyldimethoxymethylsilane, 3-methacryloyloxypropyltrimethoxysilane, 3-methacryloyloxypropyldimethoxymethylsilane, methyltris(methylethylketoximato)silane, vinyltris(methylethylketoximato)silane, methyltris(methylisobutylketoximato)silane, vinyltris(methylisobutylketoximato)silane, and the corresponding organoalkoxysilanes with ethoxy in place of the methoxy groups.

The reaction may take place in a single stage or in multiple stages. It preferably takes place in two stages.

In one preferred embodiment of the process for preparing the silane of the formula (I), in a first step, the amine of the formula (IIa) or (IIb) and optionally the amine of the formula $R^2$—NH—$R^0$ is reacted with the reagent for introducing amidine or guanidine groups, to give a hydroxyamidine or -guanidine of the formula (III),

HO-A-Z (III)

and in the second step, the hydroxy-amidine or -guanidine of the formula (III) is reacted with the alkoxysilane to give the silane of the formula (I).

A and Z here have the definitions already stated.

The reaction in the first step of the process described is carried out preferably at elevated temperature, optionally under elevated pressure, and optionally in the presence of a catalyst; elimination products released from the reagent for introducing amidine or guanidine groups, such as alcohols, esters or amines, are preferably removed during or after the reaction, in particular by means of distillation, optionally under reduced pressure.

Where the reagent used for introducing amidine groups is an orthoester of the formula $R^3$—$C(OR^a)_3$, the reaction takes place preferably at a temperature of 40 to 160° C., more particularly 60 to 140° C., and the alcohol $R^aOH$ released is removed preferably by distillation. Optionally in this case a catalyst is used, more particularly an acid.

Where the reagent used for introducing amidine groups is a 1,3-ketoester of the formula $R^3$—$C(O)CH_2C(O)OR^a$, the reaction takes place preferably at a temperature of 20 to 100° C., more particularly 40 to 80° C., and the ester $CH_3C(O)$ $OR^a$ released is removed, preferably by distillation. In this case preferably a catalyst is used, more particularly an acid, preferably a sulfonic acid.

Where the reagent used for introducing amidine groups is a nitrile of the formula $R^3$—CN, the reaction takes place preferably at a temperature of 60 to 180° C., more particularly 80 to 160° C., optionally under elevated pressure, and the ammonia released is removed, preferably by distillation. Preferably in this case a catalyst is used, more particularly a Lewis acid, preferably boron trifluoride-etherate, lithium perchlorate, zinc chloride, zinc triflate or lanthanum triflate.

Where the reagent used for introducing guanidine groups is a carbodiimide of the formula $R^5N$=C=$NR^2$, the reaction takes place preferably at a temperature of 40 to 160° C., more particularly 60 to 140° C. Optionally in this case a catalyst is used, more particularly an acid, preferably a carboxylic acid or a Lewis acid, more preferably boron trifluoride-etherate, lithium perchlorate, zinc chloride, zinc triflate or lanthanum triflate.

The ratio between the amine of the formula (IIa) or (IIb) and the reagent for introducing amidine or guanidine groups is preferably selected such that the reagent for introducing amidine or guanidine groups is converted completely in the reaction.

The reaction in the second step of the process described is carried out preferably at a temperature in the range from 20 to 160° C., and the alcohols or ketoximes released from the alkoxy- or ketoximato-silane by transesterification are preferably removed from the reaction mixture during or after the reaction, more particularly by means of distillation, optionally under reduced pressure. Here, optionally, a catalyst is used which accelerates the transesterification reaction of the alkoxy- or ketoximato-silane.

The ratio between the hydroxy-amidine or -guanidine of the formula (III) and the alkoxy- or ketoximato-silane is preferably selected such that there is not more than one hydroxyl group of the hydroxy-amidine or -guanidine to one alkoxy or ketoximato group. With particular preference the molar ratio between the hydroxyl-amidine or -guanidine of the formula (III) and the alkoxy- or ketoximato-silane is approximately 1:1.

Preferred as hydroxy-amidine of the formula (III) are reaction products of an amine of the formula (IIa) or (IIb) and optionally an amine of the formula $R^2$—NH—$R^0$ with an orthoester of the formula $R^3$—$C(OR^a)_3$ or with a 1,3-keto ester of the formula $R^3$—$C(O)CH_2C(O)OR^a$ or with a nitrile of the formula $R^3$—CN. Preferred as hydroxy-guanidine of the formula (III) are reaction products of an amine of the formula (IIa) or (IIb) with a carbodiimide of the formula $R^5N$=C=$NR^2$.

Particularly preferably the hydroxy-amidine or -guanidine of the formula (III) is selected from the group consisting of 1-(2-hydroxypropyl)-2,3-diisopropylguanidine, 1-(2-hydroxypropyl)-2,3-dicyclohexylguanidine, 1-(3-hydroxypropyl)-2,3-diisopropylguanidine, 1-(3-hydroxypropyl)-2,3-dicyclohexylguanidine, 1-(4-hydroxybutyl)-2,3-diisopropylguanidine, 1-(4-hydroxybutyl)-2,3-dicyclohexylguanidine, 1-(2-hydroxy-1,1-dimethylethyl)-2,3-diisopropylguanidine, 1-(2-hydroxy-1,1-dimethylethyl)-2,3-dicyclohexylguanidine, 1-(5-hydroxypentyl)-2,3-diisopropylguanidine, 1-(5-hydroxypentyl)-2,3-dicyclohexylguanidine, 1-(6-hydroxyhexyl)-2,3-diisopropylguanidine, 1-(6-hydroxyhexyl)-2,3-dicyclohexylguanidine, 1-(3-hydroxy-1,5,5-trimethylcyclohexylmethyl)-2,3-diisopropylguanidine, 1-(3-hydroxy-1,5,5-trimethylcyclohexylmethyl)-2,3-dicyclohexylguanidine, 1-(2-(2-hydroxyethoxy)ethyl)-2,3-diisopropylguanidine, 1-(2-(2-hydroxyethoxy)ethyl)-2,3-dicyclohexylguanidine, 1-(2-(2-(2-hydroxyethoxy)ethoxy)ethyl)-2,3-diisopropylguanidine, 1-(2-(2-(2-hydroxyethoxy)ethoxy)ethyl)-2,3-dicyclohexylguanidine, 1-(2-hydroxyethyl)-2-methyl-imidazoline, and 1-(2-hydroxyethyl)-2-methyl-1,4,5,6-tetrahydropyrimidine.

In another preferred embodiment of the process for preparing the silane of the formula (I), in a first step, the amine of the formula (IIa) or (IIb) is reacted with the alkoxy- or ketoximato-silane to give a silane of the formula (IVa) or (IVb), where

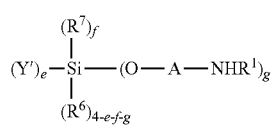

(IVa)

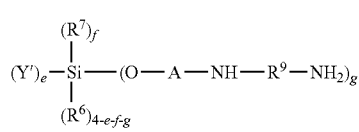

(IVb)

Y' is a monovalent hydrocarbon radical having 1 to 20 C atoms, which optionally has a terminal mercapto group, epoxide group, (meth)acryloyl group, amidine group, guanidine group, urethane group or urea group or has a terminal amino group of the formula —NHR$^{8'}$, and which optionally contains ether-oxygen or secondary amine-nitrogen, where R$^{8'}$ is a hydrogen radical or an alkyl or cycloalkyl or aralkyl radical having 1 to 8 carbon atoms or is a radical of the formula

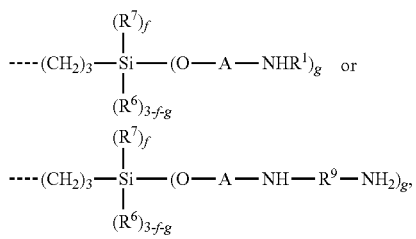

and e, f, g, A, R$^1$, R$^6$, R$^7$, and R$^9$ have the stated definitions, and in a second step, the silane of the formula (IVa) or (IVb) is reacted with the reagent for introducing amidine or guanidine groups to give the silane of the formula (I).

The reaction conditions for the reagents involved in the respective reactions here are preferably the same as for the process described via the hydroxy-amidine or -guanidine of the formula (III), with the alcohols or ketoximes released from the alkoxy- or ketoximato-silane by transesterification preferably likewise being removed from the reaction mixture during or after the reaction.

A further subject of the invention is a reaction product containing amidine or guanidine groups which is obtained from a silane of the formula (I) for which (e+f+g) is 1 or 2 or 3 by condensation with at least one compound containing silanol groups. A reaction product of this kind can be used in the same way as the silane of the formula (I) as catalyst. Preference is given to reaction products which are liquid at room temperature.

In one embodiment a reaction product of this kind is obtained solely from the silane of the formula (I) for which (e+f+g) is 1 or 2 or 3 by hydrolysis reactions and subsequent condensation reactions, and constitutes an oligomeric descendant of the silane, containing silanol and/or siloxane groups.

In another embodiment, a reaction product of this kind is obtained from the condensation of at least one silicone oil of the formula

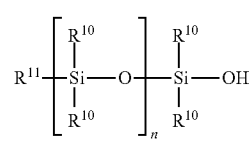

where n is an integer in the range from 3 to 200, preferably 5 to 80, more particularly 5 to 20, R$^{10}$ is a monovalent hydrocarbon radical having 1 to 6 C atoms, and R$^{11}$ is a hydroxyl radical or is an alkyl or alkoxy or ketoximato radical having 1 to 12, more particularly 1 to 6, C atoms.

The silicone oil preferably has an average molecular weight in the range from 312 to 15 000 g/mol, more particularly 460 to 6000 g/mol.

Particularly preferred are silicone oils having an average molecular weight in the range from approximately 500 to approximately 1500 g/mol.

The condensation is carried out preferably at a temperature in the range from 20 to 160° C., optionally in the presence of suitable catalysts, and the elimination product HR$^6$ released (an alcohol or ketoxime) may be removed from the reaction mixture during or after the reaction.

Preferred in this case is a ratio between the silane of the formula (I) and the silanol groups of the silicone oil at approximately 1:1.

A reaction product of this kind has, in particular, the formula (Ia),

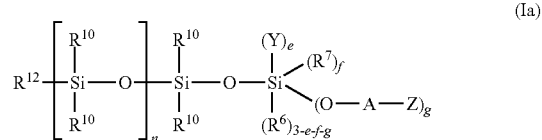

(Ia)

where

R$^{12}$ either is a hydroxyl radical or is an alkyl or alkoxy or ketoximato radical having 1 to 12, more particularly 1 to 6, C atoms, or is a radical

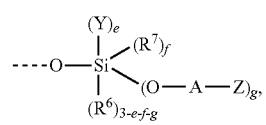

and e, f, g, n, $R^6$, $R^7$, $R^{10}$, A, and Z have the definitions already stated.

Likewise possible is the preparation of a reaction product of the formula (Ia) by first condensing the silicone oil with at least one alkoxy- or ketoximato-silane and subsequently transesterifying the resulting product with at least one hydroxyl-amidine or -guanidine of the formula (III) for which (e+f+g) is 1 or 2 or 3.

A particular feature of the silane of the formula (I) and/or of a reaction product thereof containing amidine or guanidine groups is that it exerts an accelerating effect on reactive groups, as for example isocyanate groups, epoxide groups, hydroxyl groups, amino groups or silane groups, of the kind which are present in curable compositions and are capable of crosslinking reactions with themselves or with one another. In particular it exhibits a catalytic activity in relation to the hydrolysis and condensation reaction of silane groups. It is therefore especially suitable as a catalyst for accelerating the crosslinking of curable compositions, more particularly those based on polymers containing silane groups. Since the silane of the formula (I) and/or a reaction product thereof containing amidine or guanidine groups also has a low vapor pressure, being preferably liquid, exhibits high compatibility with numerous polymers containing silane groups, and does not adversely affect the storage stability thereof, it makes it possible in particular for particularly low-emission and low-odor products to be formulated that show no tendency toward separation or migration of the catalyst.

Accordingly, the invention also relates to the use of the silane of the formula (I) or of a reaction product thereof containing amidine or guanidine groups as a catalyst in curable compositions, more particularly compositions containing silane groups, where it accelerates the crosslinking and/or curing of the composition.

Preferred as curable composition are compositions comprising at least one polymer containing silane groups, this polymer being selected more particularly from the group consisting of polyorganosiloxanes having terminal silane groups, and organic polymers containing silane groups, as described in more detail below.

A polyorganosiloxane having terminal silane groups has the advantage that in the cured state it is particularly water-resistant and light-stable and permits particularly soft-elastic properties.

An organic polymer containing silane groups has the advantage that it exhibits particularly good adhesion properties on a multiplicity of substrates and is particularly cost-effective.

For this use, the silane of the formula (I) is preferably prepared separately from the curable composition, thus not being generated in situ in the composition from a hydroxy-amidine or -guanidine of the formula (III). Here, the alcohol or ketoxime released from the alkoxy- or ketoximato-silane in the course of the transesterification is preferably removed before the silane of the formula (I) is contacted with the curable composition. A composition of this kind has the advantage that on contact with moisture it releases particularly small amounts of volatile organic compounds. Furthermore, this approach has the advantage that the silane of the formula (I) is more highly compatible in certain compositions, especially those of low polarity, than is the parent hydroxy-amidine or -guanidine of the formula (III). Moreover, before being contacted with the composition, the silane of the formula (I) can be condensed with a silicone oil to form a reaction product, this possibly being of advantage in particular in the case of compositions comprising polyorganosiloxanes having terminal silane groups, on the basis of an even better compatibility.

A further subject of the invention is therefore a composition comprising at least one silane of the formula (I) and/or at least one reaction product thereof containing amidine or guanidine groups, and at least one polymer containing silane groups.

A composition of this kind typically possesses good storability without tendency toward separation, permits a low hazard classification in view of the low toxicity and low volatility of the silane of the formula (I), and opens up the possibility of low-emission and low-odor products which cure rapidly to form a mechanically high-quality and robust material. Particularly advantageous here is the circumstance that this material exhibits virtually no propensity toward migration-related defects such as exudation or substrate soiling, in contrast to compositions comprising catalysts in accordance with the prior art, such as DBU or TMG, for example. Compositions comprising such prior-art catalysts tend toward migration effects, which may be manifested by separation prior to curing and, after curing, by sticky and/or greasy surfaces and/or instances of substrate fouling. Latter effects in particular are extremely undesirable, since sticky and greasy surfaces are quickly soiled and are difficult to paint over, and instances of substrate contamination may result in permanent discoloration.

The polymer containing silane groups is, in one preferred embodiment, a polyorganosiloxane having terminal silane groups.

One preferred polyorganosiloxane having terminal silane groups has the formula (V),

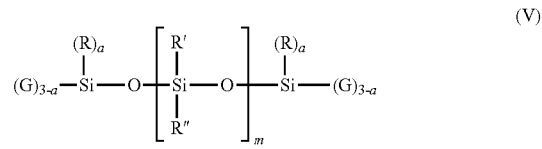

where

R, R', and R'' independently of one another are each a monovalent hydrocarbon radical having 1 to 12 C atoms;

G is a hydroxyl radical or is an alkoxy, acetoxy, ketoximato, amido or enoxy radical having 1 to 13 C atoms;

a is 0, 1 or 2; and m is an integer in the range from 50 to about 2500.

R is preferably methyl, vinyl or phenyl.

R' and R'' are preferably, independently of one another, in each case an alkyl radical having 1 to 5, preferably 1 to 3, C atoms, and more particularly are methyl.

G is preferably a hydroxyl radical or is an alkoxy or ketoximato radical having 1 to 6 C atoms, and more particularly is a hydroxyl, methoxy, ethoxy, methylethylketoximato or methylisobutylketoximato radical.

More particularly G is a hydroxyl radical.

Preferably a is 0 or 1, and more particularly is 0.

Furthermore, m is preferably selected such that the polyorganosiloxane of the formula (V) has a viscosity at room temperature in the range from 100 to 500 000 mPa·s, more particularly from 1000 to 100 000 mPa·s.

Polyorganosiloxanes of the formula (V) have good handling qualities and undergo crosslinking with moisture and/or with silane crosslinkers to form solid silicone polymers having elastic qualities.

Suitable commercially available polyorganosiloxanes of the formula (V) are available for example from Wacker, Momentive Performance Material, GE Advanced Materials, Dow Corning, Bayer or Shin Etsu.

Further to the polyorganosiloxane having terminal silane groups, the composition preferably comprises a silane crosslinker, more particularly a silane crosslinker of the formula (VI),

(VI)

where

R''' is a monovalent hydrocarbon radical having 1 to 12 C atoms,

G' is a hydroxyl radical or is an alkoxy, acetoxy, ketoximato, amido or enoxy radical having 1 to 13 C atoms; and q has a value of 0, 1 or 2, more particularly 0 or 1.

Particularly suitable silane crosslinkers of the formula (VI) are methyltrimethoxysilane, ethyltrimethoxysilane, propyltrimethoxysilane, vinyltrimethoxysilane, methyltriethoxysilane, vinyltriethoxysilane, phenyltriethoxysilane, tetramethoxysilane, tetraethoxysilane, methyltris(methylethylketoximato)silane, vinyltris(methylethylketoximato)silane and methyltris(isobutylketoximato)silane.

In a further preferred embodiment, the polymer containing silane groups is an organic polymer containing silane groups, more particularly a polyolefin, polyester, polyamide, poly(meth)acrylate or polyether or a hybrid form of these polymers, carrying in each case one or, preferably, two or more silane groups. The silane groups may be located laterally in the chain or terminally, and are bonded via a C atom to the organic polymer. With particular preference the organic polymer containing silane groups is a polyolefin containing silane groups or a polyester containing silane groups or a poly(meth)acrylate containing silane groups or a polyether containing silane groups, or a hybrid form of these polymers.

Most preferably the organic polymer containing silane groups is a polyether containing silane groups.

The silane groups of the organic polymer containing silane groups are preferably alkoxysilane groups, more particularly alkoxysilane groups of the formula (VII), where

(VII)

$R^{14}$ is a linear or branched, monovalent hydrocarbon radical having 1 to 5 C atoms, and more particularly is methyl or is ethyl or is isopropyl;

$R^{15}$ is a linear or branched, monovalent hydrocarbon radical having 1 to 8 C atoms, and more particularly is methyl or is ethyl; and x has a value of 0 or 1 or 2, preferably 0 or 1, more particularly 0.

More preferably $R^{14}$ is methyl or is ethyl.

For certain applications, the radical $R^{14}$ is preferably an ethyl group, since in that case ethanol, which is environmentally and toxicologically harmless, is released in the curing of the composition.

Particularly preferred are trimethoxysilane groups, dimethoxymethylsilane groups or triethoxysilane groups.

Methoxysilane groups here have the advantage that they are particularly reactive, and ethoxysilane groups have the advantage that they are toxicologically advantageous and particularly storage-stable.

The organic polymer containing silane groups has on average preferably 1.3 to 4, more particularly 1.5 to 3, more preferably 1.7 to 2.8 silane groups per molecule. The silane groups are preferably terminal.

The organic polymer containing silane groups preferably has an average molecular weight, determined by means of GPC relative to polystyrene standard, in the range from 1000 to 30 000 g/mol, more particularly from 2000 to 20 000 g/mol. The organic polymer containing silane groups preferably has a silane equivalent weight of 300 to 25 000 g/eq, more particularly of 500 to 15 000 g/eq.

The organic polymer containing silane groups may be solid or liquid at room temperature. It is preferably liquid at room temperature.

Most preferably the organic polymer containing silane groups is a polyether containing silane groups that is liquid at room temperature, with the silane groups being, more particularly, dialkoxysilane groups and/or trialkoxysilane groups, more preferably trimethoxysilane groups or triethoxysilane groups.

Processes for preparing polyethers containing silane groups are known to the person skilled in the art.

In one preferred process, polyethers containing silane groups are obtainable from the reaction of polyethers containing allyl groups with hydrosilanes, optionally with chain extension using, for example, diisocyanates.

In another preferred process, polyethers containing silane groups are obtainable from the copolymerization of alkylene oxides and epoxysilanes, optionally with chain extension using, for example, diisocyanates.

In a further preferred process, polyethers containing silane groups are obtainable from the reaction of polyether polyols with isocyanatosilanes, optionally with chain extension using diisocyanates.

In a further preferred process, the polyethers containing silane groups are obtainable from the reaction of polyethers containing isocyanate groups, more particularly NCO-terminated urethane-polyethers from the reaction of polyether polyols with a superstoichiometric amount of polyisocyanates, with aminosilanes, hydroxysilanes or mercaptosilanes. Polyethers containing silane groups from this process are particularly preferred. This process allows the use of a multiplicity of readily commercially available, inexpensive starting materials, allowing different polymer qualities to be obtained, such as, for example, high extensibility, high strength, a low modulus of elasticity, a low glass transition point, or a high weathering resistance.

With particular preference the polyether containing silane groups is obtainable from the reaction of NCO-terminated urethane polyethers with aminosilanes or hydroxysilanes. Suitable NCO-terminated urethane polyethers are obtainable from the reaction of polyether polyols, more particularly polyoxyalkylene diols or polyoxyalkylene triols, preferably polyoxypropylene diols or polyoxypropylene triols, with a superstoichiometric amount of polyisocyanates, more particularly diisocyanates.

The reaction between the polyisocyanate and the polyether polyol is preferably carried out in the absence of moisture at a temperature from 50° C. to 160° C., optionally in the presence of suitable catalysts, the polyisocyanate being metered such that its isocyanate groups are present in a stoichiometric excess in relation to the hydroxyl groups of the polyol. More particularly the excess polyisocyanate is selected such that the amount of free isocyanate groups in the resulting urethane polyether, after the reaction of all the hydroxyl groups, remains from 0.1 to 5 weight %, preferably 0.2 to 4 weight %, more preferably 0.3 to 3 weight %, based on the overall polymer.

Preferred diisocyanates are selected from the group consisting of 1,6-hexamethylene diisocyanate (HDI), 1-isocyanato-3,3,5-trimethyl-5-isocyanatomethylcyclohexane (i.e., isophorone diisocyanate or IPDI), 2,4- and 2,6-tolylene diisocyanate and any desired mixtures of these isomers (TDI), and 4,4'-, 2,4'-, and 2,2'-diphenylmethane diisocyanate and any desired mixtures of these isomers (MDI). Particularly preferred are IPDI or TDI. Most preferred is IPDI. In this way, polyethers containing silane groups are obtained that have particularly good light fastness.

Especially suitable as polyether polyols are polyoxyalkylene diols or polyoxyalkylene triols having a degree of unsaturation of less than 0.02 meq/g, more particularly less than 0.01 meq/g, and an average molecular weight in the range from 400 to 25 000 g/mol, more particularly 1000 to 20 000 g/mol. Besides polyether polyols, it is also possible proportionally to use other polyols, especially polyacrylate polyols, and also low molecular mass diols or triols.

Suitable aminosilanes for the reaction with an NCO-terminated urethane-polyether are primary and secondary aminosilanes. Preferred are 3-aminopropyltrimethoxysilane, 3-aminopropyldimethoxymethylsilane, 4-aminobutyltrimethoxysilane, 4-amino-3-methylbutyltrimethoxysilane, 4-amino-3,3-dimethylbutyltrimethoxysilane, N-butyl-3-aminopropyltrimethoxysilane, N-phenyl-3-aminopropyltrimethoxysilane, adducts of primary aminosilanes such as 3-aminopropyltrimethoxysilane, 3-aminopropyldimethoxymethylsilane or N-(2-aminoethyl)-3-aminopropyltrimethoxysilane and Michael acceptors such as acrylonitrile, (meth)acrylic esters, (meth)acrylamides, maleic or fumaric diesters, citraconic diesters or itaconic diesters, especially dimethyl or diethyl N-(3-trimethoxysilylpropyl)aminosuccinates. Likewise suitable are analogs of the stated aminosilanes having ethoxy or isopropoxy groups in place of the methoxy groups on the silica.

Suitable hydroxysilanes for the reaction with an NCO-terminated urethane polyether are obtainable in particular from the addition of aminosilanes onto lactones or onto cyclic carbonates or onto lactides.

Aminosilanes suitable for this purpose are, in particular, 3-aminopropyltrimethoxysilane, 3-aminopropyltriethoxysilane, 4-aminobutyltrimethoxysilane, 4-aminobutyltriethoxysilane, 4-amino-3-methylbutyltrimethoxysilane, 4-amino-3-methylbutyltriethoxysilane, 4-amino-3,3-dimethylbutyltrimethoxysilane, 4-amino-3,3-dimethylbutyltriethoxysilane, 2-aminoethyltrimethoxysilane or 2-aminoethyltriethoxysilane. Particularly preferred are 3-aminopropyltrimethoxysilane, 3-aminopropyltriethoxysilane, 4-amino-3,3-dimethylbutyltrimethoxysilane or 4-amino-3,3-dimethylbutyltriethoxysilane. Suitable lactones are, in particular, γ-valerolactone, γ-octalactone, δ-decalactone, and ε-decalactone, more particularly γ-valerolactone. Suitable cyclic carbonates are, in particular, 4,5-dimethyl-1,3-dioxolan-2-one, 4,4-dimethyl-1,3-dioxolan-2-one, 4-ethyl-1,3-dioxolan-2-one, 4-methyl-1,3-dioxolan-2-one or 4-(phenoxymethyl)-1,3-dioxolan-2-one.

Suitable lactides are, in particular, 1,4-dioxane-2,5-dione (lactide of 2-hydroacetic acid, also called "glycolide"), 3,6-dimethyl-1,4-dioxane-2,5-dione (lactide of lactic acid, also called "lactide"), and 3,6-diphenyl-1,4-dioxane-2,5-dione (lactide of mandelic acid).

Preferred hydroxysilanes which are obtained in this way are N-(3-triethoxysilylpropyl)-2-hydroxypropanamide, N-(3-trimethoxysilylpropyl)-2-hydroxypropanamide, N-(3-triethoxysilylpropyl)-4-hydroxypentanamide, N-(3-triethoxysilylpropyl)-4-hydroxyoctanamide, N-(3-triethoxysilylpropyl)-5-hydroxy-decanamide, and N-(3-triethoxysilylpropyl)-2-hydroxypropylcarbamate.

Furthermore, suitable hydroxysilanes are also obtainable from the addition of aminosilanes onto epoxides or from the addition of amines onto epoxysilanes. Preferred hydroxysilanes which are obtained in this way are 2-morpholino-4(5)-(2-trimethoxysilylethyl)cyclohexan-1-ol, 2-morpholino-4(5)-(2-triethoxysilylethyl)cyclohexan-1-ol or 1-morpholino-3-(3-(triethoxysilyl)propoxy)propan-2-ol.

Also suitable as polyethers containing silane groups are commercially available products, more particularly the following: MS Polymer™ (from Kaneka Corp.; particularly the products S203H, S303H, S227, S810, MA903, and S943); MS Polymer™ or Silyl™ (from Kaneka Corp.; especially the products SAT010, SAT030, SAT200, SAX350, SAX400, SAX725, MAX450, MAX951); Excestar® (from Asahi Glass Co. Ltd.; especially the products S2410, S2420, S3430, S3630); SPUR+* (from Momentive Performance Materials; especially the products 1010LM, 1015LM, 1050MM); Vorasil™ (from Dow Chemical Co.; especially the products 602 and 604); Desmoseal® (from Bayer MaterialScience AG; especially the products S XP 2458, S XP 2636, S XP 2749, S XP 2774, and S XP 2821), TEGOPAC® (from Evonik Industries AG; especially the products Seal 100, Bond 150, Bond 250), Polymer ST (from Hanse Chemie AG/Evonik Industries AG, especially the products 47, 48, 61, 61LV, 77, 80, 81); Geniosil® STP (from Wacker Chemie AG; especially the products E10, E15, E30, E35).

Particularly preferred organic polymers containing silane groups have end groups of the formula (VIII),

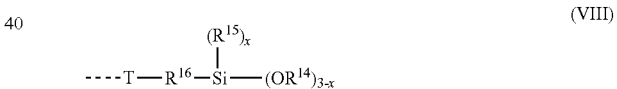

(VIII)

where $R^{16}$ is a linear or branched, divalent hydrocarbon radical having 1 to 12 C atoms, which optionally has cyclic and/or aromatic fractions and optionally has one or more heteroatoms, more particularly one or more nitrogen atoms;

T is a divalent radical selected from —O—, —S—, —N($R^{17}$)—, —O—CO—N($R^{17}$)—, —N($R^{17}$)—CO—O—, and —N($R^{17}$)—CO—N($R^{17}$)—, where $R^{17}$ is a hydrogen radical or is a linear or branched hydrocarbon radical having 1 to 20 C atoms which optionally has cyclic fractions, and which optionally has an alkoxysilane, ether or carboxylic ester group; and $R^{14}$, $R^{15}$ and x have the definitions already stated.

Preferably $R^{16}$ is 1,3-propylene or is 1,4-butylene, it being possible for butylene to be substituted by one or two methyl groups.

More preferably $R^{16}$ is 1,3-propylene.

The silane of the formula (I) is present in the composition preferably in an amount such that the concentration of amidine or guanidine groups from the silane of the formula (I), based on the amount of the crosslinkable polymer, is in the range from 0.1 to 20 mmol/100 g polymer, preferably 0.1 to 15 mmol/100 g polymer, more particularly 0.1 to 10 mmol/100 g. Such a composition exhibits high storability and rapid curing.

Further to the above-described silane of the formula (I) and/or a reaction product thereof containing amidine or guanidine groups, the composition may comprise further catalysts, especially for the crosslinking of silane groups. Suitable further catalysts are, in particular, metal compounds and/or basic nitrogen compounds or phosphorus compounds.

Suitable metal compounds are, in particular, compounds of tin, titanium, zirconium, aluminum or zinc, particularly diorganotin(IV) compounds, such as, in particular, dibutyltin(IV) diacetate, dibutyltin(IV) dilaurate, dibutyltin(IV) dineodecanoate or dibutyltin(IV) bis(acetylacetonate) and dioctyltin(IV) dilaurate, and also titanium(IV) complexes or zirconium(IV) complexes or aluminum(III) complexes or zinc(II) complexes with, in particular, alkoxy, carboxylate, 1,3-diketonate, 1,3-ketoesterate or 1,3-ketoamidate ligands.

Suitable basic nitrogen compounds or phosphorus compounds are, in particular, imidazoles, pyridines, phosphazene bases or, preferably, amines, hexahydrotriazines, biguanides, and also further amidines or guanidines.

Suitable amines are, in particular, alkyl-, cycloalkyl- or aralkylamines such as triethylamine, triisopropylamine, 1-butylamine, 2-butylamine, tert-butylamine, 3-methyl-1-butylamine, 3-methyl-2-butylamine, dibutylamine, tributylamine, hexylamine, dihexylamine, cyclohexylamine, dicyclohexylamine, dimethylcyclohexyl-amine, benzylamine, dibenzylamine, dimethylbenzylamine, octylamine, 2-ethylhexylamine, di-(2-ethylhexyl)amine, laurylamine, N,N-dimethyllaurylamine, stearylamine, N,N-dimethylstearylamine; fatty amines derived from natural fatty acid mixtures, such as, in particular, cocoalkylamine, N,N-dimethylcocoalkyl-amine, $C_{16\text{-}22}$-alkylamine, N,N-dimethyl-$C_{16\text{-}22}$-alkylamine, soyaalkylamine, N,N-dimethylsoyaalkylamine, oleylamine, N,N-dimethyloleylamine, tallowalkylamine or N,N-dimethyltallowalkylamine, obtainable for example under the trade names Armeen® (from Akzo Nobel) or Rofamin® (from Ecogreen Oleochemicals); aliphatic, cycloaliphatic or araliphatic diamines such as ethylenediamine, butanediamine, hexamethylenediamine, dodecanediamine, neopentanediamine, 2-methylpentamethylenediamine (MPMD), 2,2(4),4-trimethylhexamethylenediamine (TMD), isophoronediamine (IPD), 2,5(2,6)-bis(aminomethyl)bicyclo[2.2.1]heptane (NBDA), 1,3-xylylenediamine (MXDA), N,N'-di(tert-butyl) ethylenediamine, N,N,N',N'-tetramethylethylenediamine, N,N,N',N'-tetramethylpropylenediamine, N,N,N',N'-tetramethylhexamethylenediamine, 3-dimethylaminopropylamine, 3-(methylamino)propylamine, 3-(cyclohexylamino)propylamine, piperazine, N-methylpiperazine, N,N'-dimethylpiperazine, 1,4-diazabicyclo[2.2.2]octane, fatty polyamines such as N-cocoalkyl-1,3-propanediamine, N-oleyl-1,3-propanediamine, N-soyaalkyl-1,3-propanediamine, N-tallowalkyl-1,3-propanediamine or N—($C_{16\text{-}22}$-alkyl)-1,3-propanediamine, obtainable for example under the trade name Duomeen® (from Akzo Nobel); polyalkyleneamines such as diethylenetriamine, dipropylenetriamine, triethylenetetramine (TETA), tetraethylenepentamine (TEPA), pentamethylenehexamine (PEHA), 3-(2-aminoethyl)aminopropylamine, N,N'-bis(3-aminopropyl)ethylenediamine, N-(3-aminopropyl)-N-methylpropanediamine, bis(3-dimethylaminopropyl)amine, N-(3-dimethylaminopropyl)-1,3-propylenediamine, N-(2-aminoethyl)piperazine (N-AEP), N-(2-aminopropyl)piperazine, N,N'-di-(2-aminoethyl)piperazine, 1-methyl-4-(2-dimethylaminoethyl)piperazine, N,N,N',N",N"-pentamethyldiethylenetriamine, N,N,N',N",N"-pentamethyldipropylenetriamine, polyethyleneimines obtainable for example under the trade names Lupasol® (from BASF) and Epomin® (from Nippon Shokubai); ether amines, such as, in particular, 2-methoxyethylamine, 2-ethoxyethylamine, 3-methoxypropylamine, 3-ethoxypropylamine, 3-(2-ethylhexyloxy)propylamine, 3-(2-methoxyethoxy)propylamine, 2(4)-methoxyphenylethylamine, morpholine, N-methylmorpholine, N-ethylmorpholine, 2-aminoethylmorpholine, bis(2-aminoethyl) ether, bis(dimethylaminoethyl) ether, bis(dimorpholinoethyl) ether, N,N,N'-trimethyl-N'-hydroxyethylbis(2-aminoethyl) ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine, or 2-aminopropyl-terminated glycols, of the kind obtainable for example under the trade name Jeffamin® (from Huntsman); amino alcohols, such as, in particular, ethanolamine, isopropanolamine, diethanolamine, diisopropanolamine, triethanolamine, triisopropanolamine, N-butylethanolamine, diglycolamine, N,N-diethylethanolamine, N-methyldiethanolamine, N-methyldiisopropylamine, N,N,N'-trimethylaminoethylethanolamine, N-(3-dimethylaminopropyl)-N,N-diisopropanolamine, N,N-bis(3-dimethylaminopropyl)-N-isopropanolamine, 2-(2-dimethylaminoethoxy)ethanolamine, or adducts of mono- and polyamines with epoxides or diepoxides; amines containing phenol groups, such as, in particular, condensation products of phenols, aldehydes, and amines (so-called Mannich bases and phenalkamines) such as, in particular, 2-(dimethylaminomethyl)phenol, 2,4,6-tris(dimethylaminomethyl)phenol, or polymers of phenol, formaldehyde, and N,N-dimethyl-1,3-propanediamine, and also phenalkamines obtainable commercially under the brand names Cardolite® (from Cardolite), Aradur® (from Huntsman), and Beckopox® (from Cytec); polyamines containing amide groups, so-called polyamidoamines, of the kind available commercially, for example, under the brand names Versamid® (from Cognis), Aradur® (from Huntsman), Euretek® (from Huntsman) or Beckopox® (from Cytec); or aminosilanes, such as, in particular, 3-aminopropyltrimethoxysilane, 3-aminopropyldimethoxymethylsilane, N-(2-aminoethyl)-3-aminopropyltrimethoxysilane, N-(2-aminoethyl)-3-aminopropyl-methyldimethoxysilane, N-(2-aminoethyl)-N'-[3-(trimethoxy-silyl)propyl]ethylenediamine or their analogs with ethoxy rather than the methoxy groups on the silica.

Suitable hexahydrotriazines are, in particular, 1,3,5-hexahydrotriazine or 1,3,5-tris(3-(dimethylamino)propyl)hexahydrotriazine.

Suitable biguanides are, in particular, biguanide, 1-butylbiguanide, 1,1-dimethylbiguanide, 1-butylbiguanide, 1-phenylbiguanide or 1-(o-tolyl)biguanide (OTBG).

Suitable further amidines are, in particular, 1,8-diazabicyclo[5.4.0]undec-7-ene (DBU), 1,5-diazabicyclo[4.3.0] non-5-ene (DBN), 6-dibutylamino-1,8-diazabicyclo[5.4.0] undec-7-ene, 6-dibutylamino-1,8-diazabicyclo[5.4.0]undec-7-ene, N,N'-di-n-hexylacetamidine (DHA), 2-methyl-1,4,5,6-tetrahydropyrimidine, 1,2-dimethyl-1,4,5,6-tetrahydropyrimidine, 2,5,5-trimethyl-1,4,5,6-tetrahydropyrimidine, N-(3-trimethoxysilylpropyl)-4,5-dihydroimidazole or N-(3-triethoxysilylpropyl)-4,5-dihydroimidazole.

Suitable further guanidines are, in particular, 1-butylguanidine, 1,1-dimethylguanidine, 1,3-dimethylguanidine, 1,1,3,3-tetramethylguanidine (TMG), 2-(3-(trimethoxysilyl)propyl)-1,1,3,3-tetramethylguanidine, 2-(3-(methyldimethoxysilyl)propyl)-1,1,3,3-tetramethylguanidine, 2-(3-(triethoxysilyl)propyl)-1,1,3,3-tetramethylguanidine, 1,5,7-triazabicyclo[4.4.0]dec-5-ene (TBD), 7-methyl-1,5,7-triazabicyclo[4.4.0]dec-5-ene, 7-cyclohexyl-1,5,7-triazabicyclo[4.4.0]dec-5-ene, 1-phenylguanidine, 1-(o-tolyl)guanidine (OTG), 1,3-diphenylguanidine, 1,3-di(o-tolyl)guanidine or 2-guanidinobenzimidazole.

The composition may further comprise, as cocatalyst, an acid, more particularly a carboxylic acid. Preference is given to aliphatic carboxylic acids such as formic acid, lauric acid, stearic acid, isostearic acid, oleic acid, 2-ethyl-2,5-dimethylcapronoic acid, 2-ethylhexanoic acid, or neodecanoic acid, fatty acid mixtures from the hydrolysis of natural fats or oils, or dicarboxylic and polycarboxylic acids, especially poly(meth)acrylic acids.

The composition in one preferred embodiment is substantially free from organotin compounds. Organotin-free compositions are advantageous in terms of health protection and environmental protection. More particularly the tin content of the curable composition is less than 0.1 wt %, more particularly less than 0.05 wt %.

The composition in another preferred embodiment comprises a combination of at least silane of the formula (I) and/or a reaction product thereof containing amidine or guanidine groups, and at least one organotin compound, more particularly a diorganotin(IV) compound such as those recited above. A composition of this kind has a high cure rate even at a low tin content, this being advantageous on toxicological and environmental grounds.

In one embodiment of the invention, the composition comprises at least one organotitanate. A combination of a silane of the formula (I) and/or a reaction product thereof containing amidine or guanidine groups, and an organotitanate, exhibits particularly high catalytic activity. As a result, a composition of this kind is enabled to cure rapidly with a relatively small amount of organotitanate employed.

Suitable organotitanate comprises, in particular, titanium (IV) complex compounds.

Preferred organotitanates are selected more particularly from
- titanium(IV) complex compounds having two 1,3-diketonate ligands, more particularly 2,4-pentanedionate (=acetylacetonate), and two alkoxide ligands;
- titanium(IV) complex compounds having two 1,3-ketoesterate ligands, more particularly ethyl acetoacetate, and two alkoxide ligands;
- titanium(IV) complex compounds having one or more aminoalkoxide ligands, more particularly triethanolamine or 2-((2-aminoethyl)amino)ethanol, and one or more alkoxide ligands;
- titanium(IV) complex compounds having four alkoxide ligands;
- and also organotitanates with higher degrees of condensation, especially oligomeric titanium(IV) tetrabutoxide, also termed polybutyl titanate;
- suitable alkoxide ligands being, in particular, isobutoxy, n-butoxy, isopropoxy, ethoxy, and 2-ethylhexoxy.

Especially suitable are the commercially available products Tyzor® AA, GBA, GBO, AA-75, AA-65, AA-105, DC, BEAT, BTP, TE, TnBT, KTM, TOT, TPT or IBAY (all from Dorf Ketal); Tytan PBT, TET, X85, TAA, ET, S2, S4 or S6 (all from Borica Company Ltd.), and Ken-React® KR® TTS, 7, 9QS, 12, 26S, 33DS, 38S, 39DS, 44, 134S, 138S, 133DS, 158FS or LICA® 44 (all from Kenrich Petrochemicals).

Especially suitable organotitanates are selected from bis(ethylacetoacetato)diisobutoxytitanium(IV) (available commercially, for example, as Tyzor® IBAY from Dorf Ketal), bis(ethylacetoacetato)diisopropoxytitanium(IV) (available commercially, for example, as Tyzor® DC from Dorf Ketal), bis(acetylacetonato)diisopropoxytitanium(IV), bis(acetylacetonato)diisobutoxy-titanium(IV), tris(oxyethyl)amineisopropoxytitanium(IV), bis[tris(oxyethyl)amine]diisopropoxytitanium(IV), bis(2-ethylhexane-1,3-di-oxy)titanium(IV), tris[2-((2-aminoethyl)amino)ethoxy]ethoxytitanium(IV), bis(neopentyl(diallyl)oxy)diethoxytitanium(IV), titanium(IV)tetrabutoxide, tetra(2-ethylhexyloxy)titanate, tetra(isopropoxy)titanate, and polybutyl titanate. Most preferred are bis(ethylacetoacetato)diisobutoxytitanium(IV) or bis(ethylacetoacetato)diisopropoxytitanium(IV).

Further to the silane of the formula (I) and/or a reaction product thereof containing amidine or guanidine groups, the composition may comprise further constituents, especially the following auxiliaries and adjuvants:
- adhesion promoters and/or crosslinkers, more particularly aminosilanes such as, in particular, 3-aminopropyltrimethoxysilane, 3-aminopropyldimethoxymethylsilane, N-(2-aminoethyl)-3-aminopropyltrimethoxysilane, N-(2-aminoethyl)-3-aminopropyldimethoxymethylsilane, N-(2-aminoethyl)-N'-[3-(trimethoxysilyl)propyl]ethylenediamine or analogs thereof with ethoxy rather than methoxy groups, and also N-phenyl-, N-cyclohexyl- or N-alkylaminosilanes, mercaptosilanes, epoxysilanes, (meth)acrylosilanes, anhydridosilanes, carbamatosilanes, alkylsilanes or iminosilanes, oligomeric forms of these silanes, adducts of primary aminosilanes with epoxysilanes or (meth)acrylosilanes or anhydridosilanes, amino-functional alkylsilsesquioxanes, more particularly amino-functional methylsilsesquioxane or amino-functional propylsilsesquioxane. Especially suitable are 3-aminopropyltrimethoxysilane, 3-aminopropyltriethoxysilane, N-(2-aminoethyl)-3-aminopropyltrimethoxysilane, N-(2-aminoethyl)-3-aminopropyltriethoxysilane, 3-glycidoxypropyltrimethoxysilane, 3-glycidoxypropyltriethoxysilane or 3-ureidopropyltrimethoxysilane, or oligomer forms of these silanes;
- drying agents, more particularly tetraethoxysilane, vinyltrimethoxysilane, vinyltriethoxysilane or organoalkoxysilanes which have a functional group in α-position to the silane group, more particularly N-(methyldimethoxysilylmethyl)-O-methyl-carbamate, (methacryloxymethyl)silanes, methoxymethylsilanes, orthoformic esters, calcium oxide or molecular sieves, more particularly vinyltrimethoxysilane or vinyltriethoxysilane;
- plasticizers, more particularly trialkylsilyl-terminated polydialkylsiloxanes, preferably trimethylsilyl-terminated polydimethylsiloxanes, more particularly having viscosities in the range from 10 to 1000 mPa·s, or corresponding compounds in which some of the methyl groups are replaced by other organic groups, more particularly phenyl, vinyl or trifluoropropyl groups, so-called reactive plasticizers in the form of monofunctional, i.e., unilaterally reactive, polysiloxanes, carboxylic esters such as phthalates, more particularly dioctyl phthalate, bis(2-ethylhexyl) phthalate, bis(3-propylheptyl) phthalate, diisononyl phthalate or diisodecyl phthalate, diesters of ortho-cyclohexanedicarboxylic acid, especially diisononyl 1,2-cyclohexane-dicarboxylate, adipates, especially dioctyl adipate, bis(2-ethylhexyl)adipate, azelates, especially bis(2-ethylhexyl) azelate, sebacates, especially bis(2-ethylhexyl) sebacate or diisononyl sebacate, polyols, especially polyoxyalkylene polyols or polyester polyols, glycol ethers, glycol esters, organic phosphoric or sulfonic esters, sulfonamides, polybutenes, or fatty acid methyl or ethyl esters derived from natural fats or oils, also called "biodiesel", with plasticizers containing siloxane groups being particularly suitable for polymers containing silane groups in the form of polyorganosiloxanes;

solvents;

inorganic or organic fillers, more particularly natural, ground or precipitated calcium carbonates, optionally with a coating of fatty acids, especially stearic acid, or barite (heavy spar), talcs, finely ground quartzes, silica sand, dolomites, wollastonites, kaolins, calcine kaolins, mica (potassium aluminum silicate), molecular sieves, aluminum oxides, aluminum hydroxides, magnesium hydroxide, silicas, including finely divided silicas from pyrolysis processes, industrially produced carbon blacks, graphite, metal powders such as aluminum, copper, iron, silver or steel, PVC powders, or hollow beads;

fibers, more particularly glass fibers, carbon fibers, metal fibers, ceramic fibers or polymeric fibers such as polyamide fibers or polyethylene fibers;

dyes;

pigments, especially titanium dioxide or iron oxides;

rheological modifiers, especially thickeners, more particularly phyllosilicates such as bentonites, derivates of castor oil, hydrogenated castor oil, polyamides, polyurethanes, urea compounds, pyrogenic silicas, cellulose ethers or hydrophobically modified polyoxyethylenes;

stabilizers with respect to oxidation, heat, light or UV radiation;

natural resins, fats or oils such as roson, schellac, linseed oil, castor oil or soybean oil;

nonreactive polymers, such as, in particular, homopolymers or copolymers of unsaturated monomers, more particularly from the group encompassing ethylene, propylene, butylene, isobutylene, isoprene, vinyl acetate or alkyl (meth)acrylates, more particularly polyethylenes (PE), polypropylenes (PP), polyisobutylenes, ethylene-vinyl acetate copolymers (EVA) or atactic poly-α-olefins (APAO);

flame retardants, especially the aforementioned fillers aluminum hydroxide and magnesium hydroxide, or, in particular, organic phosphoric esters such as, in particular, triethyl phosphate, tricresyl phosphate, triphenyl phosphate, diphenyl cresyl phosphate, isodecyl diphenyl phosphate, tris(1,3-dichloro-2-propyl) phosphate, tris(2-chloroethyl) phosphate, tris(2-ethylhexyl) phosphate, tris(chloroisopropyl) phosphate, tris(chloropropyl) phosphate, isopropylated triphenyl phosphate, mono-, bis- or tris(isopropylphenyl) phosphates with different degrees of isopropylation, resorcinol bis(diphenyl phosphate), bisphenol-A bis(diphenyl phosphate) or ammonium polyphosphates;

surface-active substances, especially wetting agents, flow control agents, deaerating agents or defoamers;

biocides, especially algicides, fungicides or fungal growth inhibitors;

and also further substances customarily employed in curable compositions. It may be advisable to carry out chemical or physical drying of certain constituents before mixing them into the composition.

In one preferred embodiment the composition comprises at least one drying agent and at least one adhesion promoter and/or crosslinker.

In one preferred embodiment the composition contains no phthalate plasticizers. Such compositions are toxicologically advantageous and have fewer problems with migration effects.

The fraction of polymer containing silane groups of the composition is customarily 10 to 80 wt %, more particularly 15 to 60 wt %, preferably 15 to 50 wt %, based on the total weight of the composition.

The composition is preferably produced and stored in the absence of moisture. It is typically storage-stable in a suitable packaging or facility, such as, in particular, a bottle, a can, a pouch, a pail, a drum or a cartridge, with exclusion of moisture.

The composition may take the form of a one-pack or of a multi-pack, more particularly two-pack, composition.

A "one-pack" composition in the present document is one in which all constituents of the composition are stored in mixed form in the same container, and which is curable with moisture.

A "two-pack" composition in the present document refers to one in which the constituents of the composition are present in two different components, which are stored in containers separate from one another. Not until shortly before or during the application of the composition are the two components mixed with one another, at which point the mixed composition cures, optionally with exposure to moisture.

Where the composition comprises a polyorganosiloxane having terminal silane groups, preference is given both to a one-pack composition, also termed RTV-1, and to a two-pack composition, also termed RTV-2. In the case of an RTV-2 composition, the polyorganosiloxane having terminal silane groups is preferably a constituent of the first component, and a silane crosslinker, more particularly a silane crosslinker of the formula (VI), is preferably a constituent of the second component. The silane of the formula (I) here may be present in the first and/or in the second component.

Where the composition comprises an organic polymer containing silane groups, the composition is preferably a one-pack composition.

A second component or optionally further components is or are mixed with the first component before or during application, more particularly by way of a static mixer or a dynamic mixer.

The composition in particular is applied at ambient temperature, preferably in a temperature range between 0° C. and 45° C., more particularly 5° C. to 35° C., and also cures under these conditions.

The crosslinking reaction of the silane groups begins on application, optionally under the influence of moisture. Silane groups present may undergo condensation with silanol groups present to form siloxane groups (Si—O—Si groups). On contact with moisture, silane groups present may also undergo hydrolysis to form silanol groups (Si—OH groups) and may, through subsequent condensation reactions, form siloxane groups (Si—O—Si groups). Ultimately, as a result of these reactions, the composition cures. The silane of the formula (I) accelerates this curing.

If water is needed for the curing, it may either come from the air (atmospheric humidity), or else the composition may be brought into contact with a water-containing component, as for example by being spread-coated, with a smoothing agent for example, or by being sprayed, or the composition may be admixed on application with water or with a water-containing component, in the form for example of a water-containing or water-releasing liquid or paste. A paste is especially suitable in the event the composition itself is in the form of a paste.

In the case of curing by means of atmospheric moisture, the composition undergoes through-curing from the outside inward, with formation first of all of a skin on the surface of the composition. The skin-forming time, as it is called, represents a measure of the cure rate of the composition. The rate of curing here is determined generally by various factors, such as the availability of water, the temperature, etc., for example.

The composition is suitable for a multiplicity of applications, particularly as paint, varnish or primer, as resin for producing fiber composite material, as rigid foam, flexible foam, molding, elastomer, fiber, film or membrane, as encapsulant, sealant, adhesive, covering, coating or paint for construction and industrial applications, as for example as a seam seal, cavity seal, electrical insulation compound, filling compound, joint sealant, welded-seam or crimped-seam sealant, assembly adhesive, bodywork adhesive, glazing adhesive, sandwich element adhesive, laminating adhesive, laminate adhesive, packaging adhesive, wood adhesive, wood flooring adhesive, anchoring adhesive, floor covering, floor coating, balcony coating, roof coating, concrete protection coating, garage coating, sealing, pipe coating, anticorrosion coating, textile coating, damping element, sealing element or filling compound.

The composition is especially suitable as an adhesive and/or sealant, particularly for the sealing of joints and for elastic adhesive bonds in construction and industrial applications, and also as an elastic coating having crack-bridging properties, more particularly for protecting and/or sealing, for example, roofs, floors, balconies, parking levels or concrete pipes.

Preferably, therefore, the composition represents an adhesive or a sealant or a coating.

A composition of this kind typically comprises plasticizers, fillers, adhesion promoters and/or crosslinkers and drying agents, and optionally further auxiliaries and additives.

For application as an adhesive or sealant, the composition preferably has a pastelike consistency with pseudo plastic properties. A pastelike sealant or adhesive of this kind is applied in particular from commercial cartridges, which are operated manually or by means of compressed air or battery, or is applied from a drum or hobbock by means of a conveying pump or an extruder, optionally by means of an application robot, to a substrate.

For application as a coating, the composition preferably has a fluid consistency at room temperature, with self-modeling properties. Optionally it is slightly thixotropic, allowing the coating to be applied to sloping or vertical surfaces without immediately running away. It is applied in particular by roller or brush, or by pouring out and spreading with the aid, for example, of a roller, a scraper or a toothed trowel.

At application, the composition is preferably applied to at least one substrate. Suitable substrates are, in particular,
- glass, glass-ceramic, concrete, mortar, brick, tile, plaster or natural stones such as limestone, granite or marble;
- metals and alloys, such as aluminum, iron, steel or non-ferrous metals, and also surface-treated metals or alloys, such as galvanized or chrome-plated metals;
- leather, textiles, paper, wood, woodbase materials bound using resins, examples being phenolic resins, melamine resins or epoxy resins; resin-textile composite materials, and other so-called polymer composites;
- plastics, such as polyvinyl chloride (rigid and flexible PVC), acrylonitrilebutadiene-styrene copolymers (ABS), polycarbonate (PC), polyamide (PA), polyester, poly(methylmethacrylate) (PMMA), epoxy resins, polyurethanes (PU), polyoxymethylene (POM), polyolefins (PO), polyethylene (PE) or polypropylene (PP), ethylene/propylene copolymers (EPM) or ethylene/propylene/diene terpolymers (EPDM), or fiber-reinforced plastics such as carbon fiber-reinforced plastics (CRP), glass fiber-reinforced plastics (GRP) or sheet molding compounds (SMC), it being possible for the plastics to have been surface-treated preferably by means of plasma, corona or flame;
- coated substrates, such as powder-coated metals or alloys;
- inks or paints, especially automotive topcoat materials.

As and when required, the substrates may be pretreated before the composition is applied, such pretreatment being in particular by physical and/or chemical cleaning methods or by the application of an adhesion promoter, an adhesion promoter solution or a primer.

The composition is especially suitable for contact with substrates which are particularly sensitive to interferences from migrating substances, in particular from the formation of discoloration or spots. Particular substrates are fine-pore substrates such as marble, limestone or other natural stones, gypsum, cement mortar or concrete, but also plastics. On PVC, in particular, severe discolorations are observed in the presence of catalysts such as DBU or TMG, for example, and cannot be removed by cleaning. Such effects are not observed with the silane of the formula (I).

Adhesive bonding or sealing can be applied to two identical or two different substrates, more particularly the substrates identified above.

After the composition has been cured with water, in particular in the form of atmospheric moisture, and/or with at least one suitable crosslinker, a cured composition is obtained.

The result of the use of the composition is an article which has in particular been bonded, sealed or coated with the composition. The article more particularly is a built structure, more particularly a built structure in construction or civil engineering, or an industrially manufactured product or a consumer product, more particularly a window, a household appliance or a means of transport such as, in particular, an automobile, a bus, a truck, a rail vehicle, a ship, an aircraft or a helicopter; or the article may be an installable component thereof.

EXAMPLES

Set out below are working examples which are intended to illustrate the invention described. The invention is of course not confined to these working examples described.

"Standard conditions" refer to a temperature of 23±1° C. and a relative atmospheric humidity of 50±5%.

"EEW" stands for the epoxide equivalent weight.

$^1$H-NMR spectra were measured on a Bruker Ascend 400 spectrometer at 400.14 MHz; the chemical shifts δ are reported in ppm relative to tetramethylsilane (TMS). Coupling constants J are reported in Hz. No distinction was made between true and pseudo coupling patterns.

Infrared spectra (FT-IR) were measured on a Nicolet iS5 FT-IR instrument from Thermo Scientific, equipped with a horizontal ATR measuring unit with diamond crystal. Liquid samples were applied neat in the form of films; solid samples were dissolved in $CH_2Cl_2$. The absorption bands are reported in wavenumbers ($cm^{-1}$) (measurement window: 4000-650 $cm^{-1}$).

Gas chromatograms (GC) were measured in the temperature range from 60 to 320° C. with a heating rate of 15° C./min and 10 min residence time at 320° C. The injector temperature was 250° C. A Zebron ZB-5 column was used (L=30 m, ID=0.25 mm, dj=0.5 μm) with a gas flow rate of 1.5 ml/min. Detection was by means of flame ionization (FID), the signals being evaluated via area percent method.

The skin-forming time (SFT) was determined by applying a few grams of the composition in a layer thickness of approximately 2 mm to cardboard and measuring the time under standard conditions taken for residues no longer to remain on a pipette for the first time when the surface of the composition is contacted gently with the pipette, which is made from LDPE.

The nature of the surface was tested by tactile means.

The mechanical properties of tensile strength, elongation at break, and modulus of elasticity (at 0-5% and 0-50% elongation) were measured in accordance with DIN EN 53504 at a tensioning velocity of 200 mm/min.

Viscosities were measured on a thermostated Rheotec RC30 cone/plate viscometer (cone diameter 50 mm, cone angle 1°, cone tip/plate distance 0.05 mm, shear rate 10 $s^{-1}$).

Preparation of Hydroxy-Amidines or -Guanidines

Guanidine H1: 1-(2-(2-Hydroxyethoxy)ethyl)-2,3-diisopropylguanidine

In a round-bottomed flask, 23.14 g of 2-(2-aminoethoxy) ethanol (Diglycolamine® agent, from Huntsman) and 25.24 g of N,N'-diisopropylcarbodiimide (from Sigma-Aldrich) were mixed and the mixture was heated to 120° C. with stirring. At regular intervals the reaction mixture was analyzed by FT-IR spectroscopy. After 2 hours, the carbodiimide band at about 2120 $cm^{-1}$ had disappeared entirely. At that point the reaction mixture was freed from the volatile constituents under reduced pressure. This gave 56.50 g of a pale yellow oil of low odor.

FT-IR: 3354 (O—H), 2963, 2921, 2865, 1616 (C=N), 1524, 1465, 1362, 1337, 1178, 1121, 1066, 884, 829, 715.

Amidine H2: 1-(2-Hydroxyethyl)-2-methyl-1,4,5,6-tetrahydropyrimidine

In a round-bottomed flask, 11.91 g of N-(3-aminopropyl)-2-aminoethanol, 15.94 g of trimethylorthoacetate, and 0.32 g of lanthanum(III) trifluoromethanesulfonate were heated to 120° C. with stirring for 24 hours. At that point the reaction mixture was freed from the volatile constituents under reduced pressure and the residue was distilled under reduced pressure. This gave 14.44 g of a colorless, low-odor oil having a boiling temperature of 130 to 135° C. at 0.1 mbar, which according to GC spectrum had a 98% content of amidine A1 and which, on being left to stand at room temperature, crystallized to form a white solid.

$^1$H-NMR (CDCl$_3$): δ1.83 (quint., 2H, J=5.6, NCH$_2$CH$_2$CH$_2$N), 2.02 (s, 3H, CH$_3$), 3.24 (t, 2H, J=5.8, NCH$_2$CH$_2$OH), 3.31 (m, 4H, NCH$_2$CH$_2$CH$_2$N), 3.69 (t, 2H, J=5.7, NCH$_2$CH$_2$OH).

FT-IR: 3214, 3177, 2996, 2925, 2843, 1630, 1542, 1475, 1438, 1380, 1360, 1322, 1294, 1273, 1204, 1191, 1139, 1114, 1095, 1035, 1009, 977, 915, 875, 839, 731.

Alkoxysilanes used:

| | |
|---|---|
| AMMO | 3-Aminopropyltrimethoxysilane (Silquest ® A-1110, from Momentive) |
| VTMO | Vinyltrimethoxysilane (Silquest ® A-171, from Momentive) |
| VTEO | Vinyltriethoxysilane (Silquest ® A-151, from Momentive) |
| TEOS | Tetraethoxysilane (=tetraethyl orthosilicate) (Sigma-Aldrich) |

Preparation of a Silane of the Formula (IVa)

Silane W1: 3-Aminopropyldimethoxy-2-(2-aminoethoxy)ethoxysilane

In a round-bottomed flask, 31.00 g of 2-(2-aminoethoxy) ethanol (Diglycol-Amine® agent, from Huntsman) were mixed with 50.25 g of AMMO, the mixture was heated at 100° C. for 20 hours, and methanol was distilled off at 100 mbar. At that point the reaction mixture was concentrated on a rotary evaporator at 120° C. and 10 mbar for 2 hours. This gave 65.17 g of a colorless oil of low odor.

FT-IR: 3370, 3289, 2928, 2860, 2840, 1663, 1597, 1457, 1411, 1352, 1294, 1243, 1190, 1074, 958, 908, 858, 802, 696.

Preparation of Silanes of the Formula (I)

Silane K1: 1-(2-(2-(3-Aminopropyldimethoxysilyloxy)ethoxy)ethyl)-2,3-diisopropylguanidine In a round-bottomed flask, 2.31 g of the above-prepared guanidine H1 were mixed with 1.79 g of AMMO and the mixture was heated at 90° C. under a nitrogen atmosphere for 15 hours. At that point the reaction mixture was freed from the volatile constituents under reduced pressure. This gave 3.79 g of a pale yellow, odorless oil of low viscosity which contained the silane K1 in high purity (according to NMR analysis).

$^1$H-NMR (CDCl$_3$): δ0.66 (m, 2H, CH$_2$Si), 1.13 (d, J=6.4, 12H, NCH(CH$_3$)$_2$), 1.55 (m, 2H, CH$_2$CH$_2$Si), 2.66 (m, 2H, CH$_2$NH$_2$), 3.27 (m, 2H, NCH(CH$_3$)$_2$), 3.49-3.66 (m, 12H, SiOCH$_3$ and CH$_2$OCH$_2$CH$_2$N), 3.89 (m, 2H, CH$_2$—CH$_2$OSi).

FT-IR: 2961, 2929, 2866, 2840, 1633 (C=N), 1516, 1465, 1455, 1361, 1339, 1328, 1183, 1099, 963, 809, 715.

Silane K2: 1-(2-(2-(Vinyldimethoxysilyloxy)ethoxy) ethyl)-2,3-diisopropylguanidine In a round-bottomed flask, 1.25 g of the above-prepared guanidine H1 were mixed with 1.51 g of VTMO (vinyltrimethoxysilane) and the mixture was heated at 120° C. under a nitrogen atmosphere for 24 hours. At that point the reaction mixture was freed from the volatile constituents under reduced pressure. This gave 1.54 g of a pale yellow, odorless oil of low viscosity, which contained the silane K2 and unreacted hydroxy-guanidine H1 in a ratio of about 80:20 (according to NMR analysis).

$^1$H-NMR (CDCl$_3$) (only signals of silane K2): δ1.08-1.18 (s, 12H, NCHMe$_2$), 3.27 (m, 2H, NCHMe$_2$), 3.47-3.74 (m, 12H, SiOMe and CH$_2$OCH$_2$CH$_2$N), 3.90 (m, 2H, CH$_2$OSi), 5.83-6.17 (m, 3H, CH$_2$=CHSi).

FT-IR: 3347, 2965, 2927, 2867, 1618 (C=N), 1526, 1465, 1407, 1364, 1338, 1282, 1117, 1066, 1031, 962, 885, 752.

Silane K3: 1-(2-(2-(Vinyldiethoxysilyloxy)ethoxy) ethyl)-2,3-diisopropylguanidine In a round-bottomed flask, 1.81 g of the above-prepared guanidine H1 were mixed with 2.98 g of VTEO (vinyltriethoxysilane) and the mixture was heated at 120° C. under a nitrogen atmosphere for 48 hours. At that point the reaction mixture was freed from the volatile constituents under reduced pressure. This gave 2.77 g of a pale yellow, odorless oil of low viscosity, which contained the silane K3 and unreacted hydroxy-guanidine H1 in a ratio of about 80:20 (according to NMR analysis).

$^1$H-NMR (CDCl$_3$) (only signals of silane K3): δ1.08-1.18 (s, 12H, NCHMe$_2$), 1.30 (m, 6H, CH$_3$CH$_2$OSi), 3.27 (m, 2H, NCHMe$_2$), 3.55-3.74 (m, 6H, CH$_2$OCH$_2$CH$_2$N), 3.79-3.93 (m, 6H, CH$_3$CH$_2$OSi), 5.83-6.17 (m, 3H, CH$_2$=CHSi).

FT-IR: 3366, 2966, 2927, 2882, 1638 (C=N), 1505, 1455, 1406, 1383, 1362, 1328, 1296, 1075, 1010, 961, 782, 759, 716.

Silane K4: 1-(2-(2-(Triethoxysilyloxy)ethoxy)ethyl)-2,3-diisopropylguanidine In a round-bottomed flask, 1.24 g of the above-prepared guanidine H1 were mixed with 1.74 g of TEOS (tetraethoxysilane) and the mixture was heated at 120° C. under a nitrogen atmosphere for 24 hours. At that point the reaction mixture was freed from the volatile constituents under reduced pressure. This gave 2.16 g of a pale yellow, odorless oil of low viscosity, which contained the silane K4 and unreacted hydroxy-guanidine H1 in a ratio of about 80:20 (according to NMR analysis).

$^1$H-NMR (CDCl$_3$) (only signals of silane K4): δ1.08-1.18 (s, 12H, NCHMe$_2$), 1.30 (m, 9H, CH$_3$CH$_2$OSi), 3.27 (m, 2H, NCHMe$_2$), 3.55-3.74 (m, 6H of CH$_2$CH$_2$OCH$_2$CH$_2$N), 3.79-3.93 (m, 8H, CH$_3$CH$_2$OSi and 2H of CH$_2$CH$_2$OCH$_2$CH$_2$N).

FT-IR: 3363, 2966, 2928, 2887, 1634 (C=N), 1514, 1465, 1383, 1363, 1338, 1298, 1250, 1073, 967, 792, 712.

Silane K5: 1-(2-(3-Aminopropyldimethoxysilyloxy)ethyl)-2-methyl-1,4,5,6-tetrahydropyrimidine In a round-bottomed flask, 3.59 g of the above-prepared amidine H2 were mixed with 4.43 g of AMMO and the mixture was heated at 100° C. for 5 hours, and methanol was distilled off at 100 mbar. At that point the reaction mixture was concentrated on a rotary evaporator at 120° C. and 10 mbar for 2 hours. This gave 6.63 g of a yellow, odorless oil.

$^1$H-NMR (CDCl$_3$): δ0.67 (m, 2H, CH$_2$Si), 1.05 (s, 2H, NH$_2$), 1.55 (s, 2H, CH$_2$CH$_2$Si), 1.77-1.85 (m, 2H, N—CH$_2$—CH$_2$—CH$_2$—N), 2.0 (s, 3H, CH$_3$—C), 2.68 (s, 2H, SiCH$_2$CH$_2$CH$_2$NH$_2$), 3.20-3.37 (m, 6H, CH$_2$N), 3.57 (m, 6H, OCH$_3$), 3.84 (m, 2H, SiOCH$_2$).

FT-IR: 3269, 2924, 2838, 1617 (C=N), 1481, 1420, 1376, 1352, 1317, 1292, 1247, 1189, 1079, 1064, 1014, 942, 922, 784, 694.

Silane K6: 1-(3-(2-(2-(2,3-Diisopropylguanidino)ethoxy)ethoxy)dimethoxysilyl)-propyl-2,3-diisopropylguanidine In a round-bottomed flask, 8.24 g of the above-prepared silane W1 were mixed with 11.13 g of N,N'-diisopropylcarbodiimide and the mixture was heated to 120° C. with stirring. At regular intervals the reaction mixture was analyzed by FT-IR spectroscopy. After 11 hours, the carbodiimide band at about 2120 cm$^{-1}$ had disappeared entirely. At that point the reaction mixture was freed from the volatile constituents under reduced pressure. This gave 15.69 g of a colorless oil of low odor.

$^1$H-NMR (CDCl$_3$): δ0.7 (m, 2H, CH$_2$Si), 1.12 (d, 24H, J=6.1 Hz, CH$_3$—CHN), 1.64 (s, 2H, CH$_2$CH$_2$Si), 2.99 (m, 2H, SiCH$_2$CH$_2$CH$_2$NH), 3.26 (m, 2H, OCH$_2$CH$_2$NH), 3.48-3.65 (m, 12H, OCH$_3$ and OCH$_2$), 3.65-3.8 (m, 4H, CH$_3$CH), 3.89 (m, 2H, SiOCH$_2$).

FT-IR: 3368, 2961, 2930, 2868, 2840, 1633 (C=N), 1505, 1465, 1360, 1328, 1181, 1081, 964, 811, 712.

Preparation of Polyethers Containing Silane Groups:

Polymer STP-1:

In the absence of moisture, 1000 g of Acclaim® 12200 polyol (polyoxypropylene diol with low degree of unsaturation, from Bayer; OH number 11.0 mg KOH/g), 43.6 g of isophorone diisocyanate (IPDI; Vestanat® IPDI, from Evonik), 126.4 g of diisodecyl phthalate (DIDP), and 0.1 g of bismuth tris(neodecanoate) (10 wt % in DIDP) were heated to 90° C. with continuous stirring and left at that temperature until the amount of free isocyanate groups as determined by titrimetry had reached a stable level of 0.63 wt %. Then 63.0 g of diethyl N-(3-trimethoxysilylpropyl)aminosuccinate (adduct with 3-aminopropyltrimethoxysilane and diethyl maleate; prepared according to the details in U.S. Pat. No. 5,364,955) were mixed in and the mixture was stirred at 90° C. until free isocyanate was no longer detected by FT-IR spectroscopy. The resulting polyether, containing trimethoxysilane groups and having a silane equivalent weight of about 6880 g/eq (calculated from the initial quantities), was cooled to room temperature and stored in the absence of moisture.

Polymer STP-2:

In the absence of moisture, 1000 g of Acclaim® 12200 polyol (polyoxypropylene diol with low degree of unsaturation, from Bayer; OH number 11.0 mg KOH/g), 43.6 g of isophorone diisocyanate (IPDI; Vestanat® IPDI, from Evonik), 126.4 g of diisodecyl phthalate (DIDP), and 0.1 g of bismuth tris(neodecanoate) (10 wt % in DIDP) were heated to 90° C. with continuous stirring and left at that temperature until the amount of free isocyanate groups as determined by titrimetry had reached a stable level of 0.64 wt %. Then 70.6 g of diethyl N-(3-triethoxysilylpropyl)aminosuccinate (adduct with 3-aminopropyltriethoxysilane and diethyl maleate) were mixed in and the mixture was stirred at 90° C. until free isocyanate was no longer detected by FT-IR spectroscopy. The resulting polyether, containing triethoxysilane groups and having a silane equivalent weight of about 6920 g/eq (calculated from the initial quantities), was cooled to room temperature and stored in the absence of moisture.

Commercial Catalysts used and their Abbreviations:

| | |
|---|---|
| DBU | 1,8-Diazabicyclo[5.4.0]undec-7-ene (Lupragen® N 700, from BASF) |
| TMG | 1,1,3,3-Tetramethylguanidine (from Sigma-Aldrich) |
| IBAY | Bis(ethylacetoacetato)diisobutoxytitanium(IV) (Tyzor® IBAY, from Dorf Ketal) |

Compositions Based on Polymers Containing Silane Groups:

Comparative examples are marked in tables 1 to 6 with "(Ref)".

Compositions Z1 to Z9:

A composition of 96.5 g of polymer STP-1, 0.5 g of vinyltrimethoxysilane, and 3.0 g of 3-aminopropyltrimethoxysilane was combined with various catalysts in the stated amount as per table 1, and the mixture was tested for viscosity and skin-forming time (SFT) under standard conditions, before and after storage. The skin-forming time here served as a measure of the activity of the catalyst in relation to the crosslinking reaction of the silane groups, i.e., for the crosslinking rate; the change in viscosity and in the skin-forming time after storage are a measure of the storage stability. Furthermore, the applied mixture after 24 hours under standard conditions was tested to ascertain whether the surface was dry, as desired, or had formed a greasy film, this being a sign of the exudation of the catalyst on account of poor compatibility with the cured plastic, and/or as to whether the surface was tacky, this being a sign of incomplete curing. Furthermore, a film 2 mm thick was produced from the mixture, left to cure under standard conditions for 7 days, and tested for mechanical properties. The results are reproduced in tables 1 and 2. "Comp." standards for "composition".

TABLE 1

| Comp. | Catalyst | Amount | Concentration[1] | Viscosity [Pa · s] | | | SFT | |
|---|---|---|---|---|---|---|---|---|
| | | | | fresh | stored[2] | Increase | fresh | stored[2] |
| Z1 | Silane K1 | 0.69 g | 1.9 | 21.3 | 28.2 | 32% | 13' | 21' |
| Z2 | Silane K2 | 0.59 g | 1.9 | 28.8 | 35.5 | 23% | 15 | 12' |
| Z3 | Silane K3 | 0.63 g | 1.9 | 26.7 | 34.9 | 31% | 16' | 15' |
| Z4 | Silane K4 | 0.66 g | 1.9 | 27.8 | 36.1 | 30% | 14' | 11' |
| Z5 | Silane K5 | 0.53 g | 1.9 | 22.4 | 24.7 | 10% | 25' | 24' |
| Z6 | Silane K6 | 0.46 g | 1.9 | 21.8 | 36.7 | 68% | 13' | 13' |
| Z7 (Ref) | DBU | 0.28 g | 1.9 | 27.2 | 36.9 | 36% | 25' | 29' |
| Z8 (Ref) | TMG | 0.21 g | 1.9 | 22.3 | 24.6 | 10% | 65' | 75' |
| Z9 (Ref) | Amidine H2 | 0.26 g | 1.9 | 22.2 | 25.0 | 13% | 79' | 62' |

[1]mmol of amidine or guanidine groups per 100 g of polyether containing silane groups.
[2]for 7 days at 60° C. in a closed container.

TABLE 2

| Comp. | Surface after 24 h | Tensile strength | Elongation at break | Modulus of elasticity | |
|---|---|---|---|---|---|
| | | | | 0-5% | 0-50% |
| Z1 | dry | 0.75 MPa | 99% | 0.99 MPa | 0.77 MPa |
| Z2 | dry | 0.66 MPa | 84% | 1.26 MPa | 0.81 MPa |
| Z3 | dry | 0.72 MPa | 107% | 0.87 MPa | 0.77 MPa |
| Z4 | dry | 0.67 MPa | 82% | 1.30 MPa | 0.83 MPa |
| Z5 | dry | 0.77 MPa | 118% | 1.21 MPa | 0.80 MPa |
| Z6 | dry | 0.73 MPa | 103% | 1.21 MPa | 0.82 MPa |
| Z7 (Ref) | greasy | 0.58 MPa | 72% | 1.16 MPa | 0.77 MPa |
| Z8 (Ref) | sticky | 0.62 MPa | 90% | 1.19 MPa | 0.75 MPa |
| Z9 (Ref) | dry | 0.67 MPa | 90% | 1.19 MPa | 0.80 MPa |

Compositions Z10 to Z14:

A composition of 95.9 g of polymer STP-2, 0.4 g of vinyltriethoxysilane, and 3.7 g of N-(2-aminoethyl)-3-aminopropyltriethoxysilane was combined with various catalysts in the stated amount as per table 3, and the mixture, as described for composition Z1, was tested for viscosity, skin-forming time (SFT), surface nature, and mechanical properties. The results are reproduced in tables 3 and 4. "Comp." stands for "composition".

TABLE 3

| Comp. | Catalyst | Amount | Concentration[1] | Viscosity [Pa · s] | | | SFT | |
|---|---|---|---|---|---|---|---|---|
| | | | | fresh | stored[2] | Increase | fresh | stored[2] |
| Z10 | Silane K1 | 1.38 g | 3.8 | 28.1 | 33.2 | 18% | 1 h 47' | 1 h 15' |
| Z11 | Silane K3 | 1.25 g | 3.8 | 28.9 | 34.4 | 19% | 1 h 20' | 1 h 8' |
| Z12 | Silane K4 | 1.31 g | 3.8 | 28.9 | 34.6 | 20% | 2 h 25' | 1 h 10' |
| Z13 (Ref) | DBU | 0.55 g | 3.8 | 48.8 | 58.1 | 19% | 2 h 7' | 2 h 35' |
| Z14 (Ref) | TMG | 0.42 g | 3.8 | 44.5 | 53.4 | 20% | >12 h | >12 h |

[1]mmol of amidine or guanidine groups per 100 g of polyether containing silane groups.
[2]for 7 days at 60° C. in a closed container.

TABLE 4

| Comp. | Surface after 24 h | Tensile strength | Elongation at break | Modulus of elasticity | |
|---|---|---|---|---|---|
| | | | | 0-5% | 0-50% |
| Z10 | slightly tacky | 0.65 MPa | 139% | 0.73 MPa | 0.56 MPa |
| Z11 | slightly tacky | 0.65 MPa | 139% | 0.51 MPa | 0.55 MPa |
| Z12 | slightly tacky | 0.62 MPa | 123% | 0.63 MPa | 0.58 MPa |
| Z13 (Ref) | greasy, highly sticky | 0.43 MPa | 157% | 0.28 MPa | 0.28 MPa |
| Z14 (Ref) | extremely sticky | n.d. | n.d. | n.d. | n.d. | n.d. = not determined or not measurable.

Compositions Z15 to Z18:

In a planetary mixer, 36.2 g of polymer STP-1, 60.2 g of ground chalk (Omyacarb® 5 GU, from Omya), 1.2 g of thixotropic paste produced as described below, 1.2 g of vinyl trimethoxysilane, 1.2 g of 3-aminopropyltrimethoxysilane, and various catalysts were combined in the stated amount as per table 5, and the mixture was tested, as described for composition Z1, for skin-forming time (SFT), surface nature, and mechanical properties. The results are reproduced in table 5. "Comp." stands for "composition".

The thixotropic paste was produced by charging a vacuum mixer with 300 g of diisodecyl phthalate (Palatinol® Z, from BASF) and 48 g of 4,4'-methylenediphenyl diisocyanate (Desmodur® 44 MC L, from Bayer) and gently heating the initial charge, followed by slow dropwise addition of 27 g of n-butylamine with vigorous stirring. The resulting paste was stirred for a further hour under reduced pressure and with cooling.

TABLE 5

| Comp. | Catalyst | Amount | Concentration[1] | SFT | Surface after 24 h | Tensile strength | Elongation at break | Modulus of elasticity [MPa] 0-5% | Modulus of elasticity [MPa] 0-100% |
|---|---|---|---|---|---|---|---|---|---|
| Z15 | Silane K1 | 0.15 g | 0.4 | 25' | dry | 3.0 MPa | 106% | 5.9 | 2.8 |
| Z16 | Silane K3 | 0.27 g | 0.8 | 11' | dry | 2.9 MPa | 116% | 5.3 | 2.6 |
| Z17 | Silane K4 | 0.29 g | 0.8 | 17' | dry | 3.1 MPa | 103% | 5.3 | 3.0 |
| Z18 (Ref) | DBU | 0.12 g | 0.8 | 25' | slightly greasy | 2.5 MPa | 103% | 6.1 | 2.8 |

[1]mmol of amidine or guanidine groups per 100 g of composition.

Compositions Z19 to Z22:

In a planetary mixer, 36.2 g of polymer STP-2, 60.2 g of ground chalk (Omyacarb® 5 GU, from Omya), 1.2 g of thixotropic paste produced as described for composition Z15, 1.2 g of vinyl triethoxysilane, 1.2 g of 3-aminopropyltriethoxysilane, and various catalysts were combined in the stated amount as per table 6, and the mixture was tested, as described for composition Z1, for skin-forming time (SFT), surface nature, and mechanical properties. The results are reproduced in table 6. "Comp." stands for "composition".

TABLE 6

| Comp. | Catalyst | Amount | Concentration[1] | SFT | Surface after 24 h | Tensile strength | Elongation at break | Modulus of elasticity [MPa] 0-5% | Modulus of elasticity [MPa] 0-100% |
|---|---|---|---|---|---|---|---|---|---|
| Z19 | Silane K1 | 0.98 g | 2.6 | 118' | slightly tacky | 2.6 MPa | 137% | 5.6 | 2.3 |
| Z19 | Silane K3 | 0.89 g | 2.6 | 85' | almost dry | 3.1 MPa | 181% | 5.2 | 2.4 |
| Z20 | Silane K4 | 0.93 g | 2.6 | 100' | almost dry | 4.3 MPa | 156% | 5.2 | 3.1 |
| Z22 (Ref) | DBU | 0.40 g | 2.6 | 83' | slightly greasy | 2.5 MPa | 155% | 4.0 | 2.0 |

[1]mmol of amidine or guanidine groups per 100 g of polyether containing silane groups.

The invention claimed is:

1. A silane of the formula (I),

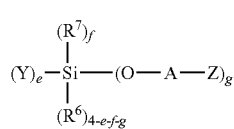

(I)

in which

Z is an amidine or guanidine group bonded via a nitrogen atom,

A is a divalent aliphatic or cycloaliphatic or arylaliphatic hydrocarbon radical having 2 to 20 C atoms, which optionally comprises ether-oxygen or secondary or tertiary amine-nitrogen, e is 0 or 1, f is 0 or 1 or 2, and g is an integer from 1 to 4, and the sum (e+f+g) is an integer from 1 to 4, $R^6$ either is an alkoxy radical having 1 to 12 C atoms which optionally contains ether-oxygen, or is a ketoximato radical having 1 to 13 C atoms, $R^7$ is a monovalent hydrocarbon radical having 1 to 12 C atoms, and Y is a monovalent hydrocarbon radical having 1 to 20 C atoms which optionally has a terminal mercapto group, epoxide group, (meth)acryloyl group, amidine group, guanidine group, urethane group or urea group or has a terminal amino group of the formula —$NHR^8$, and which optionally contains ether-oxygen or secondary amine-nitrogen, where $R^8$ is a hydrogen radical or an alkyl or cycloalkyl or aralkyl radical having 1 to 8 C atoms; or is a radical

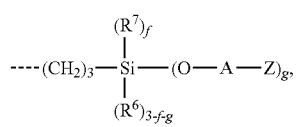

where the silane of the formula (I) contains no nitrogen atom which is bonded directly to an aromatic ring or is part of a heteroaromatic ring system.

2. The silane as claimed in claim 1, wherein Z is

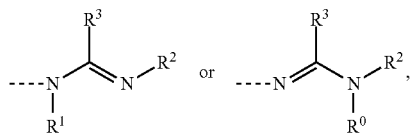

where
- R⁰ is a hydrogen radical or is an alkyl or cycloalkyl or aralkyl radical having 1 to 8 C atoms,
- R¹ is a hydrogen radical or is an alkyl or cycloalkyl or aralkyl radical having 1 to 8 C atoms, or together with R² forms R⁹,
- R² is a hydrogen radical or is an alkyl, cycloalkyl or aralkyl radical having 1 to 18 C atoms, which optionally contains ether-oxygen or tertiary amine-nitrogen, or together with R¹ forms R⁹,
- R³ is —NR⁴R⁵ or is a hydrogen radical or is an alkyl or cycloalkyl or aralkyl radical having 1 to 12 C atoms,
- R⁴ and R⁵ independently of one another are each a hydrogen radical or are an alkyl, cycloalkyl or aralkyl radical having 1 to 18 C atoms, which optionally contains ether-oxygen or tertiary amine-nitrogen, and
- R⁹ is 1,2-ethylene or 1,2-propylene or 1,3-propylene or 1,3-butylene or 1,3-pentylene, where
- R² and R⁰ may also together be an alkylene radical having 3 to 6 C atoms, which optionally contains ether-oxygen or tertiary amine-nitrogen,
- R² and R³ may also together be an alkylene radical having 3 to 6 C atoms,
- R⁴ and R⁵ may also together be an alkylene radical having 4 to 7 C atoms, which optionally contains ether-oxygen or tertiary amine-nitrogen, and
- R² and R⁵ may also together be an alkylene radical having 2 to 12 C atoms.

3. The silane as claimed in claim 2, wherein Z is

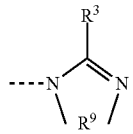

where R³ is a hydrogen radical or is an alkyl, cycloalkyl or aralkyl radical having 1 to 12 C atoms.

4. The silane as claimed in claim 2, wherein Z is

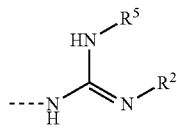

where R² and R⁵ independently of one another are each an alkyl, cycloalkyl or aralkyl radical having 1 to 12 C atoms, which optionally contains ether-oxygen or tertiary amine-nitrogen.

5. The silane as claimed in claim 1, wherein A is selected from the group consisting of 1,2-ethylene, 1,2-propylene, 1,3-propylene, 1,4-butylene, 1,1-dimethyl-1,2-ethylene, 1,5-pentylene, 1,6-hexylene, (1,5,5-trimethylcyclohexan-1-yl)methane-1,3,3-oxa-1,5-pentylene and 3,6-dioxa-1,8-octylene.

6. The silane as claimed in claim 1, wherein Y is selected from the group consisting of methyl, octyl, isooctyl, phenyl, vinyl, 3-aminopropyl, N-(2-aminoethyl)-3-aminopropyl, 3-mercaptopropyl, 3-glycidyloxypropyl, 3-acryloyloxypropyl, 3-methacryloyloxypropyl, and a radical of the formula

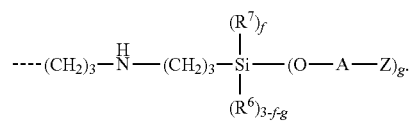

7. A process for preparing the silane as claimed in claim 1, wherein
at least one amine of the formula (IIa) or (IIb), $$HO\text{-}A\text{-}NHR^1 \quad (IIa)$$

$$HO\text{-}A\text{-}NH\text{—}R^9\text{—}NH_2 \quad (IIb)$$

optionally at least one amine of the formula R²—NH—R⁰,
at least one reagent for introducing amidine or guanidine groups, and
at least one alkoxy- or ketoximato-silane are reacted with one another.

8. A reaction product containing amidine or guanidine groups which is obtained from a silane as claimed in claim 1, wherein (e+f+g) is 1 or 2 or 3, by condensation with at least one compound containing silanol groups.

9. The reaction product as claimed in claim 8, wherein it is obtained by hydrolysis and subsequent condensation reactions solely from the silane as formula (I), wherein (e+f+g) is 1 or 2 or 3, and represents an oligomeric descendant of the silane, containing silanol and/or siloxane groups.

10. The reaction product as claimed in claim 8, wherein it is obtained from the condensation with at least one silicone oil of the formula

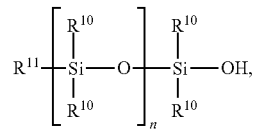

where
n is an integer in the range from 3 to 200,
R¹⁰ is a monovalent hydrocarbon radical having 1 to 6 C atoms, and
R¹¹ is a hydroxyl radical or is an alkyl or alkoxy or ketoximato radical having 1 to 13 C atoms.

11. A process for curing a curable composition comprising a step of providing, as a catalyst, the silane as claimed in claim 1 and/or a condensation product between said silane wherein (e+f+g) is 1 or 2 or 3 and at least one compound containing silanol groups.

12. The process as claimed in claim 11, wherein the curable composition comprises at least one polymer containing silane groups.

13. The process as claimed in claim 12, wherein the polymer containing silane groups is selected from the group consisting of polyorganosiloxanes having terminal silane groups and organic polymers containing silane groups.

14. A composition comprising at least one silane as claimed in claim 1 and/or at least one condensation product between said at least one silane wherein (e+f+g) is 1 or 2 or 3 and at least one compound containing silanol groups and at least one polymer containing silane groups.

15. The composition as claimed in claim 14, wherein it constitutes an adhesive or a sealant or a coating.

* * * * *